(12) United States Patent
Makino et al.

(10) Patent No.: US 7,683,077 B2
(45) Date of Patent: Mar. 23, 2010

(54) PIPERIDINE DERIVATIVE

(75) Inventors: Shingo Makino, Osaka (JP); Naoyuki Fukuchi, Kawasaki (JP); Sayaka Asari, Kawasaki (JP); Masaki Hashimoto, Kawasaki (JP); Tetsuo Yano, Kawasaki (JP); Youji Yamada, Kawasaki (JP); Munetaka Tokumasu, Kawasaki (JP); Masataka Shoji, Kawasaki (JP); Itsuya Tanabe, Kawasaki (JP); Shinichi Fujita, Kawasaki (JP); Hideki Matsumoto, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 949 days.

(21) Appl. No.: 10/557,353

(22) PCT Filed: May 19, 2004

(86) PCT No.: PCT/JP2004/007132

§ 371 (c)(1),
(2), (4) Date: Nov. 18, 2005

(87) PCT Pub. No.: WO2004/103972

PCT Pub. Date: Dec. 2, 2004

(65) Prior Publication Data

US 2007/0021460 A1    Jan. 25, 2007

(30) Foreign Application Priority Data

May 20, 2003   (JP) .............................. 2003-142296

(51) Int. Cl.
*A61K 31/445* (2006.01)
*C07D 211/08* (2006.01)
*C07D 211/22* (2006.01)
*C07D 211/20* (2006.01)

(52) U.S. Cl. ..................... 514/317; 546/192; 546/197; 546/212; 546/214; 546/221; 546/236; 514/327

(58) Field of Classification Search ................. 546/192, 546/197, 212, 214, 236, 221; 514/317, 327
See application file for complete search history.

(56) References Cited

FOREIGN PATENT DOCUMENTS

| GB | 1 542 823 | 3/1979 |
|---|---|---|
| JP | 49-32528 | 8/1974 |
| JP | 49-32540 B | 8/1974 |
| JP | 53-87367 A | 8/1978 |
| JP | 57-82369 | 5/1982 |
| JP | 59-104382 | 6/1984 |
| JP | 3-157384 A | 7/1991 |
| JP | 11-189585 | 7/1999 |
| WO | WO 9218505 A | 10/1992 |
| WO | WO 9828275 | 7/1998 |
| WO | WO 00/37082 | 6/2000 |
| WO | 2004/100952 A1 | 11/2004 |

OTHER PUBLICATIONS

Bard, J.A., et al., "Cloning of a Novel Human Serotonin Receptor (5-HT$_7$) Positively Linked to Adenylate Cyclase", *Journal of Biological Chemistry*, vol. 268, No. 31, pp. 23422-23426 (Nov. 5, 1993).
Prins, N.H., et al., "Evidence for 5-HT$_7$ receptors mediating relaxation of human colonic circular smooth muscle", *British Journal of Pharmacology*, vol. 128, pp. 849-852 (1999).
Melandri, M., et al., "Su Alcuni Nuovi N-Metil-4-Piperidil-Diaril Carbinoli Ed N-Metil-4-Piperililiden-Metani", *Boll. Chim Farm.* vol. 101, pp. 362-375 (1962).
Adham, Nika et al. "Functional Characterization of the Recombinant Human 5-Hydroxytryptamine$_{7(a)}$ Receptor Isoform Coupled to Adenylate Cyclase Stimulation", *The Journal of Pharmacol & Exp. Ther.*, vol. 287, No. 2, pp. 508-514, (1998).
Wei, Zhong-Yong et al. "N,N-Diethyl-4-(phenylpiperidin-4-ylidenemethyl)benzamide: A Novel, Exceptionally Selective, Potent Opioid Receptor Agonist with Oral Bioavailability and Its Analogues", *J. Med. Chem*, vol. 43, pp. 3895-3905, (2000).
KMN/FP6342547, EP, Jul. 23, 2008, Ajinomoto Co., Inc., European Search Report.

*Primary Examiner*—Janet L. Andres
*Assistant Examiner*—Raymond Covington
(74) *Attorney, Agent, or Firm*—The Nath Law Group; Susanne M. Hopkins; Charles D. Niebylski

(57) ABSTRACT

The present invention provides a piperidine derivative represented by the following formula or analogs thereto, which are used for agents for treating or preventing various diseases related to 5-HT7.

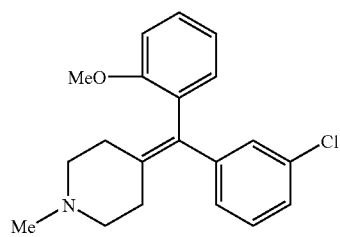

16 Claims, 1 Drawing Sheet

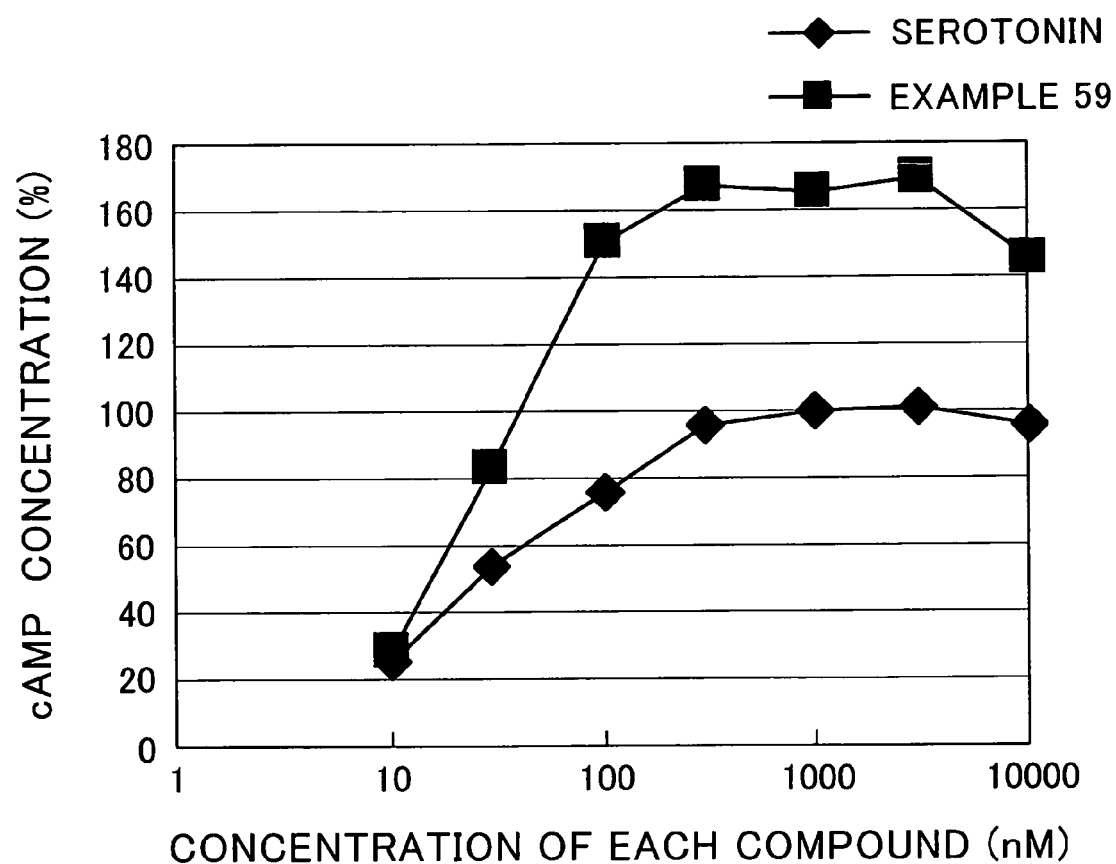

PIPERIDINE DERIVATIVE

This application is a continuation application of International Application PCT/JP2004/007132 with an international filing date of 19 May 2004 and claims priority to Japanese Patent Application No. 2003-142296 filed 20 May 2003, the entire contents of which are incorporated in their entirety.

BACKGROUND OF THE INVENTION

The present invention relates to a novel piperidine derivative and use of the piperidine derivative for pharmaceutical preparations. Abnormalities in the central 5-HT controlling function and peripheral 5-HT controlling function are considered to induce various diseases such as mental disorders, circulatory system disorders and alimentary canal dysfunction, and it has been suggested that 5-HT7 is involved in those diseases. The compounds of the present invention are advantageous because they exhibit such a high affinity for the 5-HT7 that they can act thereon as any of an agonist, partial agonist or antagonist, and therefore, they can serve as the drugs for treating or preventing the above-mentioned diseases.

As the social environments have become more and more complicated recent years, lots of people are subject to excessive stresses. This situation has increased the number of patients suffering from the irritable bowel syndrome characterized by the leading symptoms such as abnormal bowel movement, abdominal pain and the like. To alleviate such symptoms, many drugs are used, for example, anticholinergics, laxatives, antidiarrheals, drugs for controlling intestinal functions, paralyzant acting on the mucous membranes, drugs for controlling gastrointestinal motility, autonomics, herbal medicines, anxiolytic agents, antidepressants, hypnotics, antipsychotic agents and the like.

The visceral pain and abdominal pain, which are usually important biological information that can transmit the visceral and abdominal pathoses to the individual include not only the pains appearing as the symptoms associated with the above-mentioned bowel disease, that is, irritable bowel syndrome, but also the pains caused by sudden contraction and convulsion of the tube-shaped organs such as stomach, gallbladder and the like and inflammation of the peritoneum and pleura. Antispasmodics and anti-inflammatory agents are used to reduce the latter pains.

However, the above-mentioned drugs are not necessarily satisfactory in light of their insufficient clinical efficacy and some side effects. Accordingly, there is an increasing demand for development of a drug of a new type capable of exhibiting excellent therapeutic effects without any side effect.

Serotonin (5-hydroxytryptamine, 5-HT) plays an important role in the physiological or ethological processes. In particular, 90% of 5-HT exists in the enterochromaffin cells, so that the actions of 5-HT in the intestinal tract are physiologically and pathophysiologically significant. Fourteen types of 5-HT receptors have been identified up to date. The 5-HT7 receptor is the latest one among those 5-HT receptors, and expression of the 5-HT7 in the peripheral tissues of the coronal blood vessel and intestinal tract is reported (for example, see J. Biol. Chem., 268, pp 23422 (1993)).

The 5-HT7 receptor forms a conjugated system with G protein (Gs) that works to promote the production of cyclic adenosine monophosphate (cAMP). Therefore, stimulation of the serotonin leads to the increase in cAMP concentration in the cells via the 5-HT7 receptor (refer to, for example, J. Pharmacol. Exp. Ther., 287, pp 508 (1998)). As a result, for example, relaxation reaction is observed in the intestinal smooth muscle (refer to, for example, British J. Pharmacol., 128, pp 849 (1999)). In light of the above-mentioned background, it is reported that the 5-HT7 receptor antagonist has the potential for effectively treating various diseases considered to result from the abnormal conditions in the central and peripheral 5-HT controlling functions, for example, mental disorders (manic-depressive psychosis, anxiety, schizophrenia, epilepsy, somnipathy, disorders of biorhythm, migraine and the like); circulatory system disorders (hypertension and the like); and dysfunction of alimentary canal, as disclosed in, for example, Japanese Patent Unexamined Publication (JP Kokai) Hei 11-189585. Further, the therapeutic effects in a model of cerebral artery occlusion in rats are disclosed in, for example, WO200037082. In consideration of the presence of the 5-HT7 receptor on the intestinal tract tissues, some compounds having an affinity for the 5-HT7 hold promise of showing effectiveness against the irritable bowel syndrome, abdominal pain or visceral pain, and the like which are accompanied by the abnormal movement of the alimentary canal induced by the stimulation of serotonin.

However, no compound has been practically used for the treatments at the present stage on the grounds of lack of absorption by oral administration, problems in pharmacokinetics, and so on.

The scope of the present invention does not include the following compounds (i) through (iv) which are shown in British Patent Publication No. 1542823, U.S. Pat. No. 3,759,928, International Patent Publication WO 9218505, U.S. Pat. No. 3,687,956, International Patent Publication WO 9828275, Boll. Chim. Farm., 101, pp 365-375 (1962), and J. Med. Chem., 43, (21), pp 3895-3905 (2000). The compounds described in the above-mentioned references are different from those of the present invention in the mechanism and the target diseases.

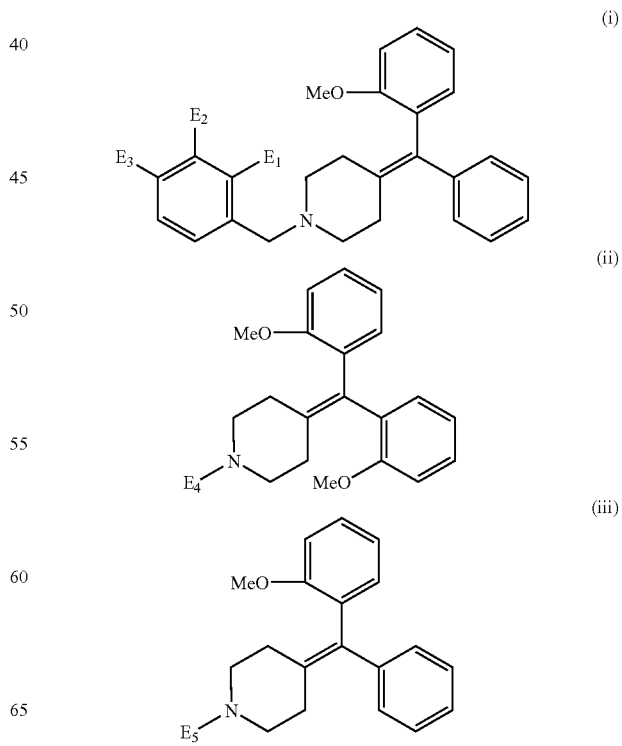

-continued (iv)

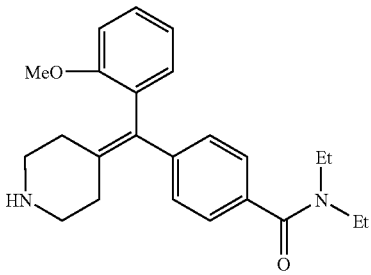

wherein
(i) $E_1$ is H—, HO— or PhCOO—, $E_2$ is H—, HO— or PhCOO—, and $E_3$ is H—, HO—, PhCOO— or tert-butyl;
(ii) $E_4$ is methyl group or propylene group having a substituent at the 3-position;
(iii) $E_5$ is HO—$CH_2CH_2$—, HO—$CH_2CH_2OCH_2CH_2$—, or H—; and
(iv) compound represented by formula (iv).

DISCLOSURE OF INVENTION

An object of the present invention is to provide a novel compound having an affinity for 5-HT7.

Another object of the present invention is to provide a pharmaceutical composition containing the above-mentioned novel compound.

Further, an object of the present invention is to provide an agent for treating or preventing the irritable bowel syndrome.

Also, an object of the present invention is to provide an agent for treating or preventing the abdominal pain and visceral pain.

To solve the above-mentioned problems, the inventors of the present invention synthesized a variety of piperidine derivatives and examined the affinity of those derivatives for the 5-HT7. As a result, it was found that particular novel phenylalanine derivatives, in particular, compounds of the following formula (1) wherein $R^2$ is a lower alkyl group such as methyl group exhibit a high affinity for the 5-HT7. The present invention has been thus accomplished on the above-mentioned findings.

Accordingly, the present invention provides a piperidine derivative represented by the following formula (1) and pharmaceutically acceptable salt thereof:

(1)

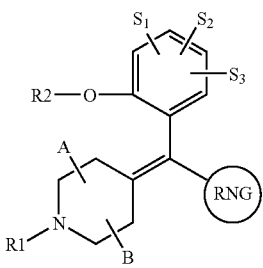

wherein $S_1$, $S_2$ and $S_3$, which may be the same or different, are each hydrogen atom, a halogen atom, hydroxyl group, lower alkyl group, lower alkenyl group, lower alkynyl group, cyclic alkyl group which may have a hetero atom in the ring thereof, aryl group, heteroaryl group, lower alkyl group substituted by cyclic alkyl group which may have a hetero atom in the ring thereof, lower alkyl group substituted by aryl group, lower alkyl group substituted by heteroaryl group, lower alkoxyl group, lower alkylthio group, lower alkoxyl group substituted by cyclic alkyl group which may have a hetero atom in the ring thereof, lower alkylthio group substituted by cyclic alkyl group which may have a hetero atom in the ring thereof, lower alkoxyl group substituted by aryl group, lower alkylthio group substituted by aryl group, lower alkoxyl group substituted by heteroaryl group, lower alkylthio group substituted by heteroaryl group, cyclic alkyloxy group which may have a hetero atom in the ring thereof, aryloxy group, heteroaryloxy group, hydroxy-lower alkyl group, hydroxy-lower alkenyl group, hydroxy-lower alkoxyl group, halogenated lower alkyl group, halogenated lower alkoxyl group, halogenated lower alkylthio group, halogenated lower alkenyl group, nitro group, cyano group, substituted or unsubstituted amino group, carboxyl group, lower alkyloxycarbonyl group, substituted or unsubstituted carbamoyl group, lower alkanoyl group, aroyl group, lower alkylsulfonyl group, or substituted or unsubstituted sulfamoyl group; or $S_1$, $S_2$ and $S_3$ may form a ring in combination, which may contain one or two hetero atoms such as oxygen atom, nitrogen atom, sulfur atom and the like in the ring thereof;

RNG is a substituted or unsubstituted aryl group, or a substituted or unsubstituted heteroaryl group containing one, two, three or four hetero atoms selected from the group consisting of oxygen atom, sulfur atom and nitrogen atom;

$R^1$ is hydrogen atom; hydroxyl group; lower alkyl group; lower alkenyl group; lower alkynyl group; cyclic alkyl group which may have a hetero atom in the ring thereof; aryl group; heteroaryl group; lower alkyl group substituted by cyclic alkyl group which may have a hetero atom in the ring thereof; lower alkyl group substituted by aryl group; lower alkenyl group substituted by aryl group; lower alkyl group substituted by heteroaryl group; lower alkyl group substituted by lower alkoxyl group; lower alkyl group substituted by amino group; lower alkyl group substituted by carboxyl group; lower alkyl group substituted by carbonyl group which is substituted by lower alkoxyl group; lower alkoxyl group; hydroxy-lower alkyl group; hydroxy-lower alkenyl group; hydroxy-lower alkyl group substituted by aryl group; halogenated lower alkyl group; halogenated lower alkenyl group; lower alkyl group substituted by amide group, which may be substituted by cyclic alkyl group where a hetero atom may be included in the ring thereof, aryl group, heteroaryl group, lower alkyl group, lower alkynyl group, lower alkoxyl group, lower alkyl group substituted by aryl group, lower alkyl group substituted by heteroaryl group, lower alkenyl group substituted by aryl group, lower alkenyl group substituted by heteroaryl group, lower alkynyl group, cyclic alkenyl group or piperonyl group; lower alkyl group substituted by sulfonamide group, which may be substituted by cyclic alkyl group where a hetero atom may be included in the ring thereof, aryl group, heteroaryl group, lower alkyl group, lower alkynyl group, lower alkoxyl group, lower alkyl group substituted by aryl group, lower alkyl group substituted by heteroaryl group, lower alkenyl group substituted by aryl group, lower alkenyl group substituted by heteroaryl group, lower alkynyl group, cyclic alkenyl group or piperonyl group; or lower alkyl group substituted by urea group, which may be substituted by cyclic alkyl group where a hetero atom may be included in the ring thereof, aryl group, heteroaryl group, lower alkyl group, lower alkynyl group, lower alkoxyl group, lower alkyl group substituted by aryl group, lower alkyl group substituted by heteroaryl group, lower alkenyl group substituted by aryl group, lower alkenyl group substituted by heteroaryl group, lower alkynyl group, cyclic alkenyl group or piperonyl group;

$R^2$ is lower alkyl group, lower alkenyl group, lower alkynyl group, halogenated lower alkyl group, halogenated lower alkenyl group, or halogenated lower alkynyl group; and A and B, which may be the same or different, are each hydrogen atom, a halogen atom or lower alkyl group, provided that the following compounds (i) through (iv) are excluded:

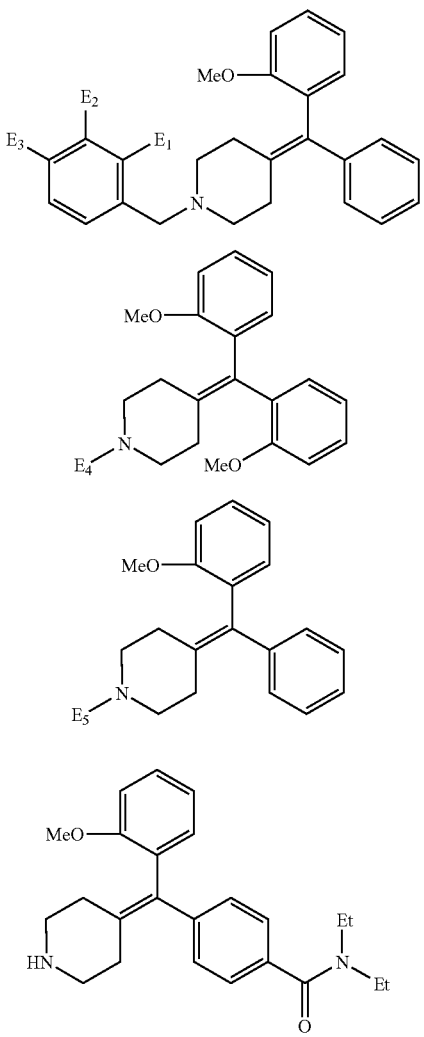

wherein (i) $E_1$ is H—, HO— or PhCOO—; $E_2$ is H—, HO— or PhCOO—; and $E_3$ is H—, HO—, PhCOO— or tert-butyl;

(ii) $E_4$ is methyl group or propylene group having a substituent at the 3-position;

(iii) $E_5$ is HO—CH$_2$CH$_2$—, HO—CH$_2$CH$_2$OCH$_2$CH$_2$—, or H—; and (iv) compound is resented by formula (iv).

Furthermore, the present invention provides compounds with an affinity for the 5-HT7, containing as the active substance the above-mentioned piperidine derivative or pharmaceutically acceptable salt thereof.

Further, the present invention provides an agent containing as the active substance the above-mentioned piperidine derivative or pharmaceutically acceptable salt thereof for treating or preventing the irritable bowel syndrome.

Further, the present invention also provides an agent containing as the active substance the above-mentioned piperidine derivative or pharmaceutically acceptable salt thereof for treating or preventing the visceral pain or abdominal pain.

BRIEF DESCRIPTION OF DRAWING

FIG. 1 is a graph showing the results of measurement of the 5HT-7 agonist activity using 5HT-7 expression cells.

BEST MODE FOR CARRYING OUT THE INVENTION

The term "lower" in the lower alkyl or the like used herein means a group having 1 to 6 carbon atoms. The alkyl group, alkenyl group and alkynyl group, each of which may also be used as the component for alkoxyl group, alkylthio group, alkanoyl group, alkylamino group and the like, may be straight-chain or branched chain. When each of the substituents shown below is used as a component of other groups, the definition for the substituent is applicable.

Examples of the alkyl group include methyl group, ethyl group, propyl group, isopropyl group, butyl group, isobutyl group, sec-butyl group, tert-butyl group, pentyl group, and hexyl group. The alkyl group may preferably have 1 to 6 carbon atoms, more preferably 1 to 4 carbon atoms. Examples of the alkenyl group include vinyl group, propenyl group, butenyl group, and pentenyl group. The alkenyl group may preferably have 2 to 6 carbon atoms, more preferably 2 to 4 carbon atoms. Examples of the alkynyl group include ethynyl group, propynyl group, and butynyl group. The alkynyl group may preferably have 2 to 6 carbon atoms, more preferably 2 to 4 carbon atoms. The cyclic alkyl group includes substituted or unsubstituted cyclic alkyl groups, for example, cyclopropyl group, cyclobutyl group, cyclopentyl group, cyclohexyl group, norbornyl group, adamantyl group, cyclohexenyl group and the like. The cycloalkyl group may preferably have 3 to 8 carbon atoms, more preferably 3 to 5 carbon atoms. Examples of the alkoxyl group include methoxy group, ethoxy group, propyloxy group, isopropyloxy group, and phenoxy group. The hetero atoms include nitrogen, oxygen, sulfur and the like. The number of carbon atoms may preferably be 1 to 6, more preferably 1 to 4. The halogen atoms include fluorine, chlorine, bromine and iodine. Examples of the halogenated alkyl group include chloromethyl group, trichloromethyl group, trifluoromethyl group, trifluoroethyl group, and pentafluoromethyl group. Examples of the halogenated alkoxyl group include trichloromethoxy group and trifluoromethoxy group. Examples of the hydroxyalkyl group include hydroxymethyl group and hydroxyethyl group. The hydroxyl group may be bonded at any position with no limitation. The cyclic alkyl group which may have a hetero atom in the ring thereof may be substituted or unsubstituted. Examples of the cyclic alkyl group include cyclopentyl group, cyclohexyl group, piperidyl group, piperazinyl group, morpholinyl group, pyrrolidinyl group, tetrahydrofuranyl group, and uracil group. The cyclic alkyl group may preferably be 4- to 8-membered ring, more preferably 5- to 7-membered ring.

The aryl group used herein means a monocyclic, dicyclic or tricyclic aromatic hydrocarbon group having 6 to 14 carbon atoms, which may have a substituent. There can be given as examples of the aryl group phenyl group, 1-naphthyl group, 2-naphthyl group and the like, preferably phenyl group and substituted phenyl group. In this case, preferably used as the substituent are a halogen atom, alkoxyl group, alkyl group, hydroxyl group, halogenated alkyl group and halogenated alkoxyl group; more preferably, a halogen atom and alkyl group; and further preferably, chlorine atom and methyl group. The heteroaryl group means a 5- to 8-membered monocyclic, dicyclic or tricyclic aromatic heterocyclic group having 1 to 4 hetero atoms on the ring thereof, selected from the group consisting of oxygen atom, sulfur atom and nitrogen atom, which heteroaryl group may have a substituent. Examples of the heteroaryl group include pyridyl group, pyrazyl group, pyrimidyl group, pyrazolyl group, pyrrolyl group, triazyl group, furyl group, thienyl group, isoxazolyl group, isothiazolyl group, indolyl group, quinolyl group, isoquinolyl group, and benzimidazolyl group. Of those groups, preferably employed are pyridyl group, pyrazyl group, pyrimidyl group, furyl group, thienyl group, substituted pyridyl group, substituted furyl group, substituted thienyl group, and the like. In this case, a halogen atom, alkoxyl group, alkyl group, hydroxyl group, halogenated alkyl group and halogenated alkoxyl group are preferably used as the substituent. Examples of the lower alkyl group substituted by aryl group include substituted or unsubstituted benzyl group and substituted or unsubstituted phenethyl group. In this case, a halogen atom, alkoxyl group, alkyl group, hydroxyl group, halogenated alkyl group and halogenated alkoxyl group are preferably used as the substituent. As the lower alkyl group substituted by heteroaryl group there can be employed pyridylmethyl group. In this case, a halogen atom, alkoxyl group, alkyl group, hydroxyl group, halogenated alkyl group and halogenated alkoxyl group are preferably used as the substituent. Examples of the alkanoyl group include formyl group, acetyl group, propanoyl group, butanoyl group, and pivaloyl group. The aroyl group includes substituted or unsubstituted benzoyl group and substituted or unsubstituted pyridylcarbonyl group. In this case, a halogen atom, alkoxyl group, alkyl group, hydroxyl group, halogenated alkyl group and halogenated alkoxyl group are preferably used as the substituent. The halogenated alkanoyl group includes trichloroacetyl group, trifluoroacetyl group and the like. The alkylsulfonyl group includes methanesulfonyl group, ethanesulfonyl group and the like. The arylsulfonyl group includes benzenesulfonyl group, p-toluenesulfonyl group and the like. The heteroarylsulfonyl group includes pyridylsulfonyl group and the like. The halogenated alkylsulfonyl group includes trifluoromethanesulfonyl group and the like. Examples of the alkyloxycarbonyl group include methoxycarbonyl group, ethoxycarbonyl group, and tert-butoxycarbonyl group. Examples of the aryl-substituted alkoxycarbonyl group include benzyloxycarbonyl group and 9-fluorenylmethoxycarbonyl group. Examples of the substituted carbamoyl group are methylcarbamoyl group, phenylcarbamoyl group, substituted phenylcarbamoyl group and the like, where a halogen atom, alkoxyl group, alkyl group, hydroxyl group, halogenated alkyl group and halogenated alkoxyl group are preferably used as the substituent. Examples of the substituted thiocarbamoyl group are methylthiocarbamoyl group, phenylthiocarbamoyl group, substituted phenylthio-carbamoyl group and the like, where a halogen atom, alkoxyl group, alkyl group, hydroxyl group, halogenated alkyl group and halogenated alkoxyl group are preferably used as the substituent. Examples of the substituent for the substituted amino group used herein include lower alkyl group, lower alkyl group substituted by aryl group, lower alkyl group substituted by heteroaryl group, lower alkanoyl group, aroyl group, halogenated lower alkanoyl group, lower alkylsulfonyl group, arylsulfonyl group, heteroarylsulfonyl group, halogenated alkylsulfonyl group, lower alkyloxycarbonyl group, aryl-substituted lower alkyloxycarbonyl group, substituted or unsubstituted carbamoyl group, and substituted or unsubstituted thiocarbamoyl group.

In the above formula (1), $R^2$ may preferably be a lower alkyl group or halogenated lower alkyl group; more preferably, methyl group, ethyl group or propyl group; and most preferably, methyl group or halogenated methyl group.

In the above formula (1), $S_1$, $S_2$ and $S_3$ may be the same or different and may preferably be hydrogen atom, a halogen atom, hydroxyl group, lower alkyl group, lower alkenyl group, lower alkynyl group, lower alkoxyl group, lower alkylthio group, hydroxy-lower alkyl group, hydroxy-lower alkenyl group, hydroxy-lower alkoxyl group, halogenated lower alkyl group, halogenated lower alkoxyl group, halogenated lower alkylthio group, halogenated lower alkenyl group, or substituted or unsubstituted amino group; more preferably, hydrogen atom, a halogen atom, lower alkyl group, lower alkoxyl group, lower alkylthio group, halogenated lower alkyl group, halogenated lower alkoxyl group or halogenated lower alkylthio group. In this case, $R^2$ may preferably represent a lower alkyl group or halogenated lower alkyl group; more preferably, methyl group or halogenated methyl group.

In the above formula (1), $R^1$ may preferably be hydrogen atom; lower alkyl group; lower alkenyl group; alkyl group substituted by cyclic alkyl group which may have a hetero atom in the ring thereof; lower alkyl group substituted by aryl group; lower alkenyl group substituted by aryl group; hydroxy-lower alkyl group; hydroxy-lower alkyl group substituted by aryl group; lower alkyl group substituted by lower alkoxyl group; lower alkyl group substituted by carbonyl group which is substituted by lower alkyloxy group; alkyl group substituted by carboxyl group; amino-substituted lower alkyl group; lower alkyl group which may be substituted by amide group substituted by any of cyclic alkyl group wherein a hetero atom may be included in the ring thereof, cyclic alkenyl group, aryl group, heteroaryl group, lower alkyl group, lower alkoxyl group, aryl-substituted alkyl group, heteroaryl-substituted alkyl group, aryl-substituted alkenyl group, heteroaryl-substituted alkenyl group or lower alkynyl group; or lower alkyl group substituted by sulfonamide group which may be substituted by any of halogenated lower alkyl group, aryl group or heteroaryl group.

In the above formula (1), $R^1$ may be more preferably a lower alkyl group substituted by sulfonamide group which is substituted by any of a lower alkyl group, halogenated lower alkyl group, aryl group or heteroaryl group.

Preferably, in the above formula (1), RNG may be a substituted aryl group, or a substituted or unsubstituted heteroaryl group wherein the hetero atom is sulfur. A substituted phenyl group is more preferable as the above-mentioned substituted aryl group. A substituted or unsubstituted thienyl group is more preferable as the above-mentioned heteroaryl group. As the substituent, preferably used are a halogen atom and lower alkyl group; and more preferably, chlorine atom and methyl group. The number of substituents and the bonding position thereof are not particularly limited. In particular, 3-chlorophenyl group, 3,4-dichlorophenyl group, 4-methylphenyl group, 2-thienyl group, 5-chloro-2-thienyl group and 5-methyl-2-thienyl group are preferred in the present invention.

In the above formula (1), A and B may be the same or different, and preferably represent hydrogen atom, a halogen atom, or lower alkyl group; and more preferably represent hydrogen atom.

Further, in the above formula (1), $S_1$, $S_2$ and $S_3$ may be the same or different and each preferably represent hydrogen atom, a halogen atom, lower alkyl group, lower alkoxyl group, lower alkylthio group, halogenated lower alkyl group, halogenated lower alkoxyl group, or halogenated lower alkylthio group, while $R^2$ may represent methyl group, and A and B may each represent hydrogen atom.

Among the compounds of formula (1), particularly preferable are the following piperidine derivatives:

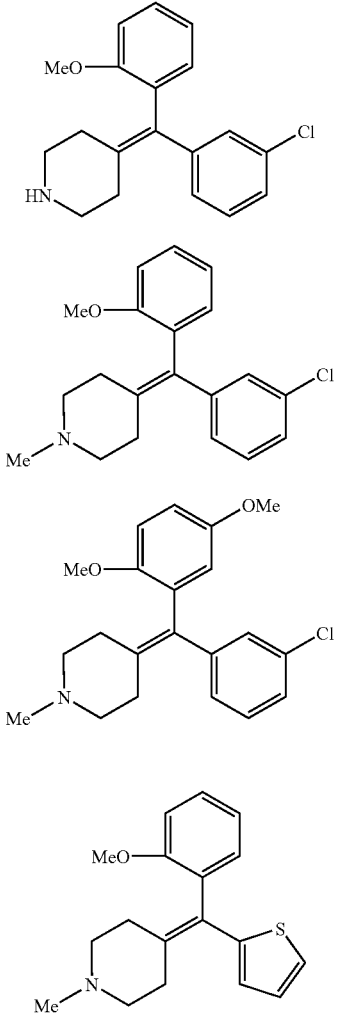

Among the compounds of formula (1), also particularly preferable is the following piperidine derivative:

Among the compounds of formula (1), also particularly preferable are the following piperidine derivatives:

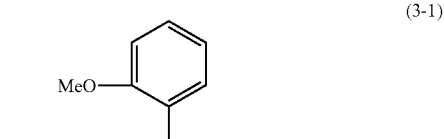

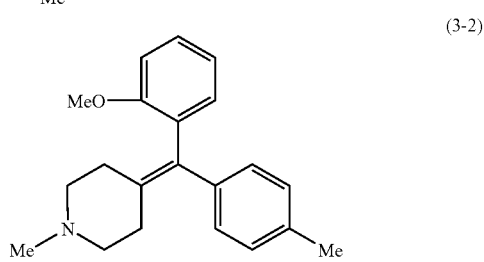

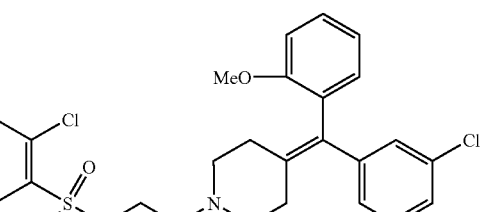

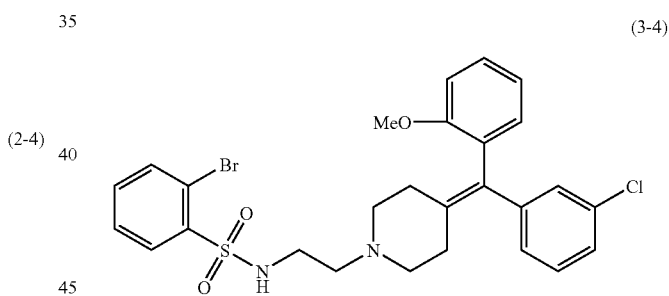

The piperidine derivative (1) represented by formula (1) according to the present invention can be prepared, for example, by the method shown below.

Reaction scheme 1

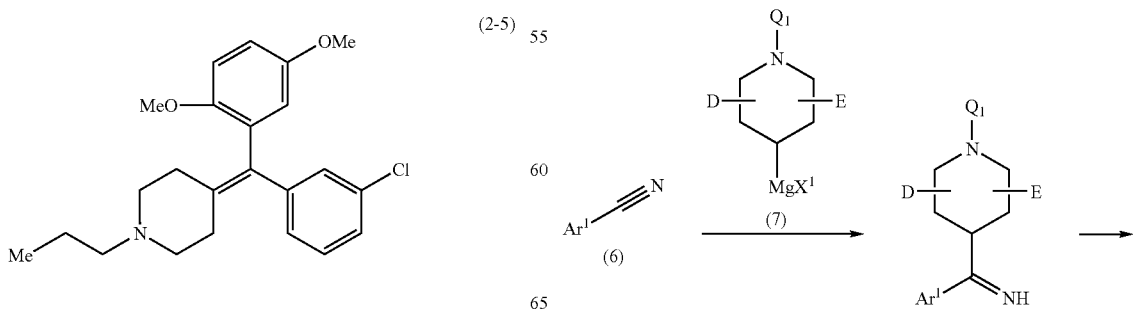

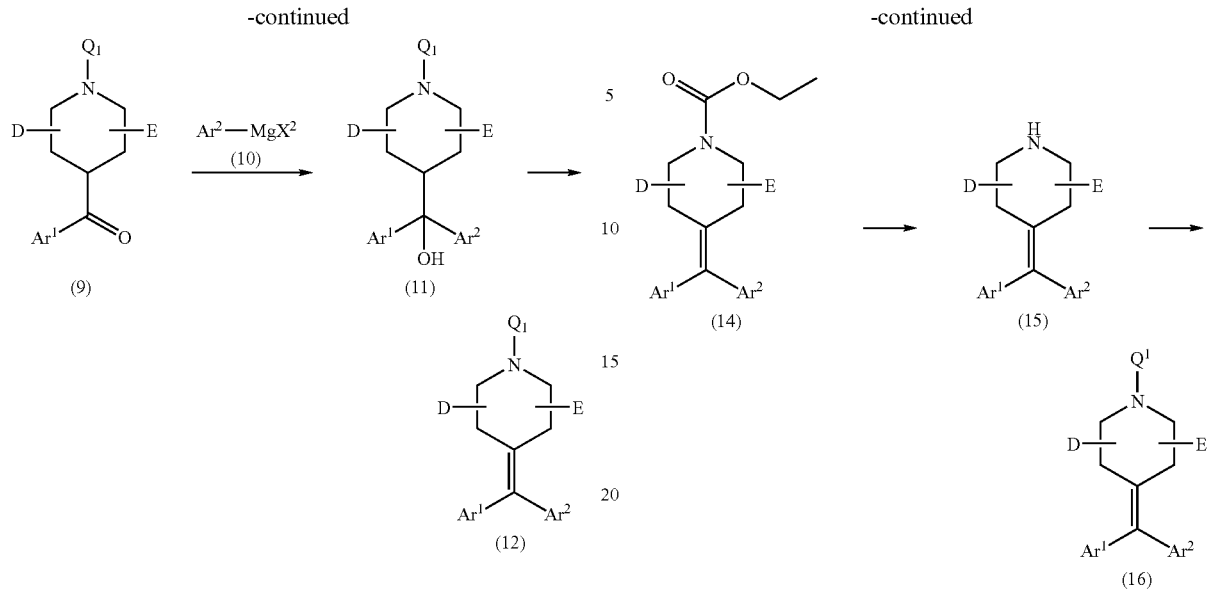

$Ar^1$ and $Ar^2$ represent an aryl group. $Ar^1$ and $Ar^2$ or $Ar^2$ and $Ar^1$ have a structure of RNG and phenyl group having substituents as shown in formula (1) respectively, or they may assume such structures that can be converted into RNG and phenyl group having substituents as shown in formula (1) respectively at any time in the course of the synthesis process. D and E have structures of A and B respectively, or may assume such structures that can be converted into A and B respectively at any time in the course of the synthesis process. $Q_1$ has a structure of $R^1$ or may assume such a structure that can be converted into $R^1$ at any time in the course of the synthesis process. $X^1$ and $X^2$, which may be the same or different, are each a halogen atom. A Grignard reagent (7) of a piperidine derivative obtainable by heating a mixture of a halogenated aromatic compound and magnesium under reflux in THF is reacted overnight with an aromatic compound having nitrile group (6) in THF at room temperature or by the application of heat under reflux, thereby obtaining an imine (8). The imine (8) thus obtained is treated under acidic conditions, to obtain a ketone (9). The ketone (9) is then allowed to react with a Grignard reagent (10) obtainable by reacting a halogenated aromatic compound and magnesium in THF, thereby obtaining a compound (11). The compound (11) is reacted with a strong acid such as sulfuric acid or the like in a mixed solvent containing methanol and the like at room temperature or under application of heat, thereby causing beta-elimination to obtain a compound (12).

Reaction scheme 2

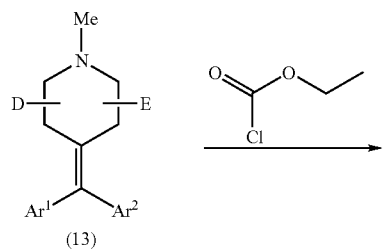

D, E, $Ar^1$, $Ar^2$ and $Q^1$ have the same definitions as in the reaction scheme 1. A compound (13) and ethyl chloroformate are heated under reflux in a solvent such as toluene or the like to obtain a compound (14). Then, the compound (14) is hydrolyzed, for example, by heating under reflux in a solvent such as n-butanol or the like using a base such as potassium hydroxide or the like, so that a compound (15) is obtained. Thereafter, the compound (15) is subjected to alkylation using various alkyl halides to obtain a compound (16).

Reaction scheme 3

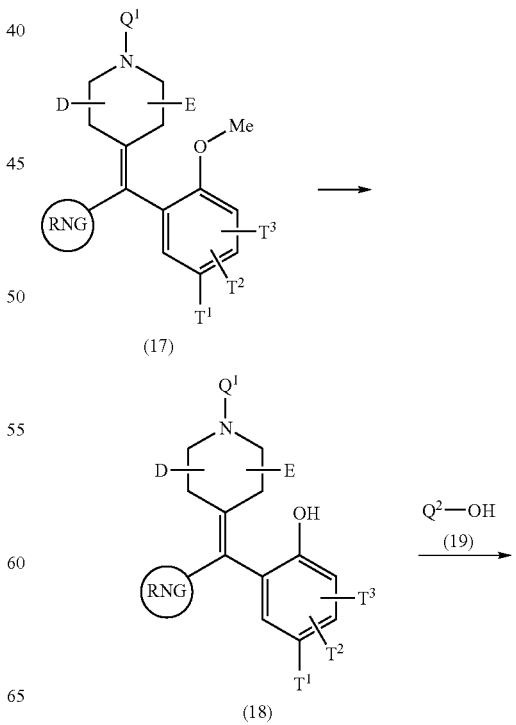

-continued

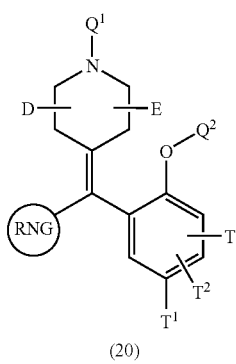

(20)

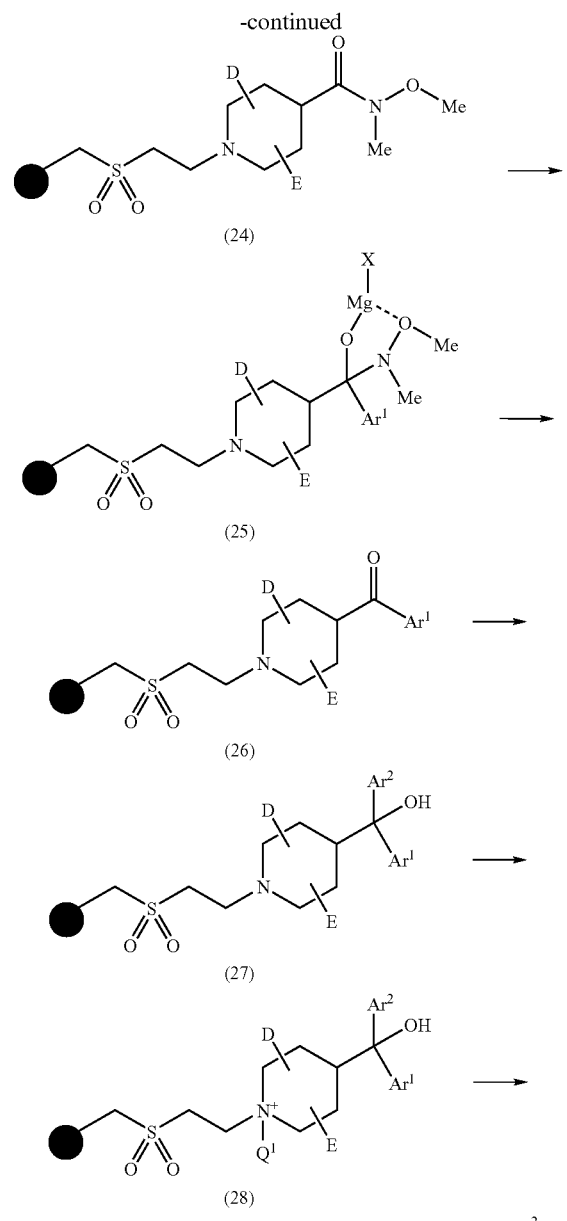

D, E, Ar¹, Ar² and Q¹ have the same definitions as in the reaction schemes 1 and 2. T¹ has a structure of S¹ as shown in formula (1) or may assume such a structure that can be converted into T¹ as shown in formula (1) at any time in the course of the synthesis process. T² and T³ have structure of S² and S³ as shown in formula (1) respectively or may assume such structures that can be converted into S² and S³ as shown in formula (1) respectively at any time in the course of the synthesis process. Q² has a structure of R² as shown in formula (1) or may assume such a structure that can be converted into R² as shown in formula (1) at any time in the course of the synthesis process. The compound (17) is treated with an acid such as BBr₃ or the like using a solvent such as dichloromethane or the like to obtain a compound (18). Then, the compound (18) is alkylated using an alkyl halide or the like, or using an alcohol (19), phosphine such as triphenyl phosphine, and an azo compound such as DEAD, DIAD, TMAD or the like according to the Mitsunobu reaction. A compound (20) can be thus obtained.

Alternatively, piperidine derivative according to the present patent application can be synthesized by the following method based on a solid-phase synthesis.

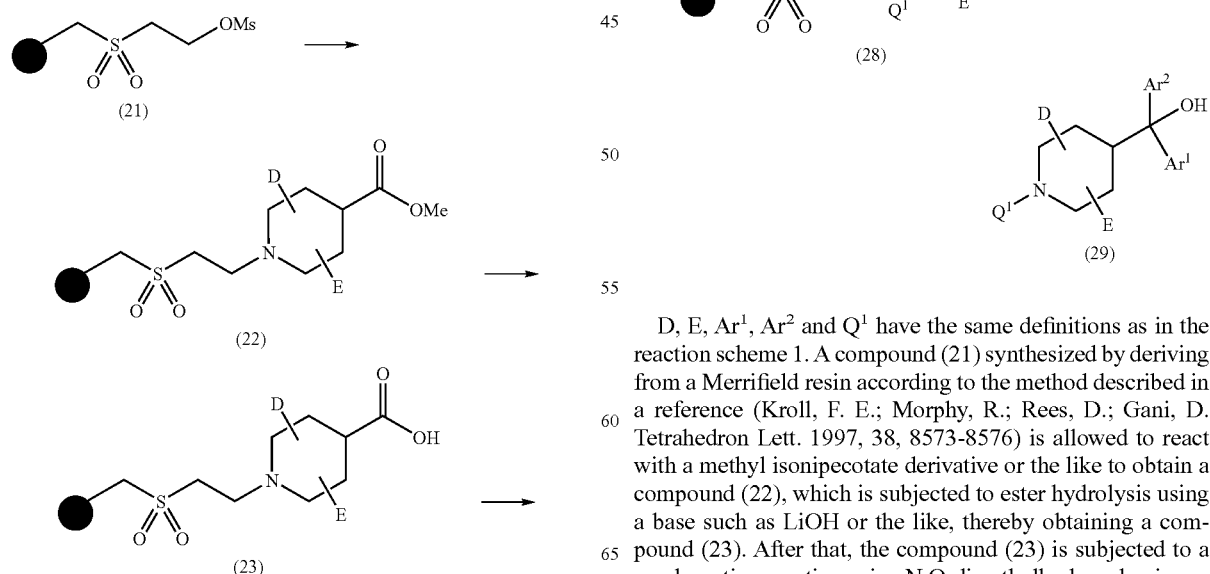

D, E, Ar¹, Ar² and Q¹ have the same definitions as in the reaction scheme 1. A compound (21) synthesized by deriving from a Merrifield resin according to the method described in a reference (Kroll, F. E.; Morphy, R.; Rees, D.; Gani, D. Tetrahedron Lett. 1997, 38, 8573-8576) is allowed to react with a methyl isonipecotate derivative or the like to obtain a compound (22), which is subjected to ester hydrolysis using a base such as LiOH or the like, thereby obtaining a compound (23). After that, the compound (23) is subjected to a condensation reaction using N,O-dimethylhydroxylamine or the like, a condensing agent such as DIC or the like, and a condensing aid such as HOAt or the like, so that a compound (24) is obtained. Thereafter, the compound (24) is reacted with a Grignard reagent to obtain a compound (25). The compound (25) is then treated with acetic acid or the like to obtain a compound (26). The compound (26) is reacted with a Grignard reagent (26) which may be the same or different from the one as used before to obtain a compound (27). The compound (27) is allowed to react with an alkyl halide or the like in a solvent such as NMP, DMF or the like, thereby obtaining a compound (28). The compound (28) is treated overnight under basic conditions, for example, using ammonia gas, so that a compound is separated from the resin by Hofmann elimination. The compound thus obtained is eluted using a solvent such as acetonitrile, dichloromethane or the like, so that a compound (29) can be obtained. Alternatively, the compound (29) can be obtained by reacting overnight the compound (28) and a solution prepared by dissolving lithium hydroxide in a mixed solvent of THF and water. Further, by inducing beta-elimination based on the method shown in the reaction scheme 1, piperidine derivative according to the present patent application can be obtained from the compound (29).

In the case where the compound represented by formula (1) according to the present invention can be turned into salts, any salts are suitable so long as they are pharmaceutically acceptable. For example, when an acidic group such as carboxyl group or the like is present in the formula, it is possible to form ammonium salts; alkali metal salts with alkali metals such as sodium, potassium and the like; alkaline earth metal salts with alkaline earth metals such as calcium, magnesium and the like; aluminum salts; zinc salts; salts with organic amines such as triethylamine, ethanolamine, morpholine, piperidine, dicyclohexylamine and the like; salts with basic amino acids such as arginine, lysine, and the like. When a basic group is present in the formula, it is possible to form salts with inorganic acids such as hydrochloric acid, sulfuric acid, phosphoric acid and the like; salts with organic carboxylic acids such as acetic acid, citric acid, benzoic acid, maleic acid, fumaric acid, tartaric acid, succinic acid and the like; and salts with organic sulfonic acids such as methanesulfonic acid, p-toluenesulfonic acid and the like. To form the salts, the compound of formula (1) is mixed with the required acid or base at a proper amount ratio in a solvent or dispersant. Alternatively, a desired salt may be obtained from another salt form by cation exchange or anion exchange.

The compounds represented by formula (1) according to the present invention include solvates, e.g., hydrates, alcohol adducts thereof, and the like.

The compounds represented by formula (1) according to the present invention or salts thereof are administered as it is, or after prepared into various pharmaceutical compositions. Those pharmaceutical compositions may be administered in a dosage form, for example, tablet, powder, pill, granule, capsule, suppository, solution, sugar-coated pill (or tablet), depot preparation, or syrup, which can be formed using conventional adjuvants in accordance with the conventional methods.

For example, the tablet can be produced by mixing an active substance, that is, a phenylalanine derivative of the present invention, with the adjuvants known in the art, e.g., inactive diluents such as lactose, calcium carbonate, calcium phosphate and the like; binders such as gum arabic, corn starch, gelatin and the like; swelling agents such as alginic acid, corn starch, pregelatinized starch and the like; sweeteners such as sucrose, lactose, saccharin and the like; flavoring agents such as peppermint, gaultheria leaves oil, cherry and the like; lubricating agents such as magnesium stearate, talc, carboxymethyl cellulose and the like; excipients for soft gelatin capsules and suppositories, such as fat, wax, semi-solid and liquid polyol, natural oil, hardened oil and the like; and excipients for solutions, such as water, alcohol, glycerol, polyol, sucrose, invert sugar, glucose, vegetable oil and the like.

The piperidine derivative including as the active substance the compound represented by formula (1) or the salt thereof, or the pharmaceutically acceptable salts of the piperidine derivative can be used for agents for treating or preventing the diseases associated with the 5-HT7, for example, functional gastrointestinal disorders including gastrointestinal tract motor disorders, e.g., irritable bowel syndrome, rumination syndrome, globus syndrome, functional heartburn, chest pain of presumed esophageal origin, functional gastrointestinal injury, functional dysphagia, functional vomiting, dysphagia, aerophagia, functional constipation, functional abdominal bloating, functional abdominal pain syndrome, functional diarrhea, sphincter of Oddi dysfunction, gallbladder dysfunction, levator ani syndrome, functional fecal incontinence, pelvic floor dyssynergia, discutient anorectal pain, pediatric gastrointestinal disorders (infant regurgitation, infant rumination syndrome, cyclic vomiting syndrome, functional dyspepsia, irritable bowel syndrome, functional abdominal pain, paroxysmal abdominal pain, aerophagia, functional diarrhea, infant dyschezia, functional constipation, functional fecal retention, functional non-retentive fecal soiling and the like), abdominal pain, visceral pain and the like. In particular, the present invention can be used for the agents for treating or preventing any of the irritable bowel syndrome. The present invention can also be used for the agents for treating or preventing any of the pathologic conditions related to the 5-HT7, for example, diseases accompanied by symptoms similar to those of the functional gastrointestinal disorders, such as neurotic disorders including anxiety disorder (panic disorder and generalized anxiety disorder), somatoform disorder, dissociative disorder, mood disorder and the like, bulimia nervosa, anorexia nervosa, sleeping disorder, diabetic gastroenteropathy and the like; or digestive disorders after surgical operation of the abdomen.

The term "irritable bowel syndrome" used herein is one of the functional gastrointestinal disorders and shows chronic or recurrent dysfunction of the gastrointestinal tract, the cause of which cannot be explained on the theory of organic abnormality or biochemical abnormality. The irritable bowel syndrome is characterized by the symptom that the abnormal bowel movements accompanied by abdominal pain and discomfort last beyond a certain period of time. According to the abnormal bowel patterns, there are three groups: "constipation type", "diarrhea type" and "alternate type" where diarrhea and constipation appear alternately (Rome II; the functional gastrointestinal disorders, 2nd Ed, Degnon Associates, McLean (2000)).

The term "visceral pain" used herein is referred to as the pain occurring in the internal organs such as the stomach, intestinal tract, heart and the like, and the peritoneum and pleura (Textbook of Pain, 4nd Ed, 603-709, Churchill Livingstone, Hartcourt Publishers Limited (1999)).

The term "abdominal pain" used herein is chronic or acute pain perceived in the abdomen region (Textbook of Pain, 4nd Ed, 603-619, Churchill Livingstone, Hartcourt Publishers Limited (1999)).

The term "pharmaceutical composition for treating the irritable bowel syndrome" used herein is effective not only in treating the irritable bowel syndrome, but also in alleviating and preventing the irritable bowel syndrome.

The term "pharmaceutical composition for treating the visceral pain" used herein is effective not only in treating the visceral pain, but also in alleviating and preventing the visceral pain.

The term "pharmaceutical composition for treating the abdominal pain" used herein is effective not only in treating the abdominal pain, but also in alleviating and preventing the abdominal pain.

In the treatments of the above-mentioned disorders, the compound of the present invention can be used alone or in combination with other drugs such as anticholinergics, laxatives, antidiarrheals, drugs for controlling intestinal function, paralyzant acting on the mucous membranes, drugs for controlling gastrointestinal motility, autonomics, herbal medicines, anxiolytic agents, antidepressants, hyphotics, antipsychotic agents, serotonin antagonists, serotonin agonists, and the like. Further, the compound of the present invention is excellent in the pharmacological action, and in addition the stable metabolism can be ensured.

The dosage for the above-mentioned purposes may be determined depending upon the targeted therapeutic effects, administration manner, treatment period, age, body weight and the like. The oral or parenteral administration rout is used. Usually, the adult dose is 1 µg to 5 g per day in oral administration; while 0.01 µg to 1 g per day in a parenteral administration.

EXAMPLES

The present invention will now be explained in detail by referring to the following examples. These examples are for the purpose of illustrating preferred embodiments of this invention, and are not to be construed as limiting the scope of the invention in any way.

Example 1

Step 1

To a reaction vessel where the atmosphere was replaced with argon, N-methyl-4-chloropiperidine (100 g), magnesium (22 g) and THF (50 mL) were added, and the resultant mixture was heated under reflux using an oil bath. Once an exothermic reaction was observed, the oil bath was removed, and vigorous stirring was continued until the exothermic reaction was completely terminated. After the reaction system was brought to room temperature (over a period of about one hour), 3-chlorobenzonitrile (100 g) was added and the resultant mixture was heated under reflux for 2 hours. After the reaction system was cooled to 0° C. using an ice bath, 100 ml of water was gradually added and subsequently 12N hydrochloric acid solution (1 L) was gradually added to the mixture. Then, the reaction solvent was eliminated under reduced pressure. With the addition of a solution prepared by mixing water (500 mL) and sodium hydroxide (500 g), the reaction mixture was thoroughly stirred and the reaction solvent was again eliminated under reduced pressure. With the addition of ethyl acetate (500 mL), the reaction mixture was sufficiently stirred, and thereafter the target ethyl acetate solution was separated by repeating the procedure for decantation 10 times. The whole ethyl acetate solution thus obtained was concentrated to obtain the desired compound as a crude product. The product was purified by silica gel chromatography, thereby obtaining 53 g of the desired compound.

Step 2

In a reaction vessel where the atmosphere was replaced with argon, 2-methoxybromobenzene (10 g) was added to a mixture of magnesium (23 g) and THF (400 mL) with vigorously stirring. Stirring was continued until an exothermic reaction was initiated. Thereafter, 2-methoxybromobenzene (140 g) was further added with due attention to the use of an ice bath and the rate of addition of 2-methoxybromobenzene. After the reaction system was brought to room temperature, the compound (34 g) synthesized in the Step 1 of Example 1 was added and the resultant mixture was stirred for 3 hours. After water (100 mL) was gradually added, 12N hydrochloric acid solution (500 mL) was gradually added to the mixture. Then, the reaction solvent was eliminated under reduced pressure. The reaction mixture was thoroughly stirred with the addition of a solution prepared by mixing water (500 mL) and sodium hydroxide (500 g), and the reaction solvent was again eliminated under reduced pressure. With the addition of ethyl acetate (500 mL), the reaction mixture was sufficiently stirred, and thereafter the ethyl acetate solution was separated by repeating the procedure for decantation 10 times. The whole ethyl acetate solution thus obtained was concentrated to obtain the desired compound.

Step 3

The compound obtained in the Step 2 of Example 1 was dissolved in a solution previously obtained by mixing concentrated sulfuric acid (24 mL) and methanol (60 mL). The resultant mixture was heated to 50° C. for 3 hours. The above-mentioned concentrated sulfuric acid solution containing the target compound was brought to room temperature and then gradually added to a solution prepared by mixing water (50 mL) and sodium hydroxide (40 g) and cooled using an ice bath. The mixture was extracted with two 300 mL portions of ethyl acetate, and thereafter the resultant solution was concentrated to obtain the desired compound as a crude product. Further, the product was purified by silica gel chromatography, thereby obtaining 17 g of the compound shown in Table.

Example 2

Step 1

The compound (11 g) synthesized in Example 1 was dissolved in toluene (50 mL). After chloroethyl formate (20 mL) was gradually added to the above toluene solution, the resultant mixture was heated under reflux for 5 hours. After 20 mL of water was added, the reaction mixture was extracted with ethyl acetate (200 mL), and thereafter the resultant organic phase was concentrated under reduced pressure, so that the desired compound was obtained as a crude product. The product was purified by silica gel chromatography, thereby obtaining 12 g of the desired compound.

Step 2

Potassium hydroxide (6.75 g) and n-butanol (51 mL) were added to the total amount of the compound obtained in the Step 1 of Example 2, and the resultant mixture was heated under reflux for 3 hours. After n-butanol was removed from the reaction mixture under reduced pressure, the mixture was extracted by the addition of ethyl acetate (100 mL) and water (50 mL). The separating organic phase was dried over magnesium sulfate and concentrated under reduced pressure, to obtain 10 g of the compound shown in Table.

Example 3

The compound (2 g) obtained in the Step 1 of Example 1 was allowed to react with a Grignard reagent at room temperature for 2 hours, which Grignard reagent was prepared by vigorously stirring 2,5-dimethoxybromobenzene (4.5 g) and magnesium (0.5 g). Water (100 ml) was gradually added and thereafter 12N hydrochloric acid solution (150 mL) was gradually added to the reaction mixture. Then, the reaction solvent was removed under reduced pressure. The reaction mixture was thoroughly stirred with the addition of a solution prepared by mixing water (150 mL) and sodium hydroxide (150 g), and the reaction solvent was again removed under reduced pressure. With the addition of ethyl acetate (150 mL), the reaction mixture was sufficiently stirred, and thereafter the ethyl acetate solution was separated by repeating the procedure for decantation 10 times. The whole ethyl acetate solution thus obtained was concentrated. The compound thus obtained was dissolved in a solution previously obtained by mixing concentrated sulfuric acid (6 mL) and methanol (15 mL), and the mixture was heated to 50° C. for 3 hours. The above-mentioned concentrated sulfuric acid solution containing the target compound was brought to room temperature and then gradually added to a solution prepared by mixing water (30 mL) and sodium hydroxide (20 g) and cooled using an ice bath. The mixture was extracted with two 150 mL portions of ethyl acetate, and thereafter the resultant solution was concentrated to obtain the desired compound as a crude product. Further, the product was purified by silica gel chromatography, thereby obtaining 2.1 g of the compound shown in Table.

Example 4

Step 1

The compound (1 g) synthesized in Example 3 was dissolved in toluene (5 mL). After chloroethyl formate (2 mL) was gradually added to the above toluene solution, the resultant mixture was heated under reflux for 4 hours. After 20 mL of water was added, the reaction mixture was extracted by adding ethyl acetate (50 mL). The resultant organic phase was concentrated under reduced pressure, so that the desired compound was obtained as a crude product. The product was purified by silica gel chromatography, thereby obtaining 2.1 g of the desired compound.

Step 2

Potassium hydroxide (1.7 g) and n-butanol (10 mL) were added to the total amount of the compound obtained in the Step 1 of Example 4, and the resultant mixture was heated under reflux for 3 hours. After n-butanol was removed from the reaction mixture under reduced pressure, the mixture was extracted by the addition of ethyl acetate (20 mL) and water (10 mL). The separating organic phase was dried over magnesium sulfate and concentrated under reduced pressure, to obtain 0.9 g of the compound shown in Table.

Example 5

Step 1

To a reaction vessel where the atmosphere was replaced with argon, N-methyl-4-chloropiperidine (15 g), magnesium (3.3 g) and THF (50 mL) were added and the resultant mixture was heated under reflux using an oil bath. Once an exothermic reaction was observed, the oil bath was removed, and vigorous stirring was continued until the exothermic reaction was completely terminated. After the reaction system was brought to room temperature (over a period of about one hour), 2-methoxybenzonitrile (100 g) was added and the resultant mixture was heated overnight under reflux. After the reaction system was cooled to 0° C. using an ice bath, 10 ml of water was gradually added and subsequently 12N hydrochloric acid solution (100 mL) was gradually added to the mixture. Then, the reaction solvent was removed under reduced pressure. The reaction mixture was thoroughly stirred with the addition of a solution prepared by mixing water (50 mL) and sodium hydroxide (50 g), and the reaction solvent was again removed under reduced pressure. With the addition of ethyl acetate (50 mL), the reaction mixture was sufficiently stirred, and thereafter the target ethyl acetate solution was separated by repeating the procedure for decantation 10 times. The whole ethyl acetate solution thus obtained was concentrated to obtain the desired compound as a crude product. The product was purified by silica gel chromatography, thereby obtaining 4 g of the desired compound.

Step 2

In a reaction vessel where the atmosphere was replaced with argon, the compound (1.2 g) obtained in the Step 1 of Example 5 was added to a Grignard reagent in THF (50 mL), the Grignard reagent being prepared by vigorously stirring 2-bromothiophene and magnesium (1 g). The resultant mixture was stirred for 3 hours. Water (10 ml) was gradually added and subsequently 12N hydrochloric acid solution (50 mL) was gradually added to the reaction mixture. Then, the reaction solvent was removed under reduced pressure. The reaction mixture was thoroughly stirred with the addition of a solution prepared by mixing water (50 mL) and sodium hydroxide (50 g), and the reaction solvent was again removed under reduced pressure. With the addition of ethyl acetate (50 mL), the reaction mixture was sufficiently stirred, and thereafter the ethyl acetate solution was separated by repeating the procedure for decantation 10 times. The whole ethyl acetate solution thus obtained was concentrated to obtain the desired compound.

Step 3

The compound obtained in the Step 2 of Example 4 was dissolved in a solution previously obtained by mixing concentrated sulfuric acid (8 mL) and methanol (20 mL), and the resultant mixture was heated to 50° C. for 3 hours. The concentrated sulfuric acid solution was brought to room temperature, and then gradually added to a solution prepared by mixing water (20 mL) and sodium hydroxide (20 g) and cooled using an ice bath. The mixture was extracted with two 150 mL portions of ethyl acetate, and thereafter the resultant solution was concentrated to obtain the desired compound as a crude product. Further, the product was purified by silica gel chromatography, thereby obtaining 1 g of the compound shown in Table.

Example 6

A mixture of the compound (82 mg) synthesized in Example 2, n-propyl bromide (31 µL), acetonitrile (2 mL) and potassium carbonate (80 mg) was stirred overnight at room temperature. The purification was carried out in the same manner as in the Step 2 of Example 4, thereby obtaining the target compound (70 mg).

Examples 7 to 25

Using the alkyl halides and reaction conditions shown in Table 2, the target compounds were obtained in the same manner as in Example 6.

Example 26

The compound (4 g) obtained in Example 2 was allowed to react overnight with (2-bromo-ethyl)-carbamic acid tert-butyl ester (5.7 g) in the presence of triethylamine (5.34 mL) in acetonitrile (50 mL) at room temperature. The purification was carried out in the same manner as in the Step 2 of Example 4, thereby obtaining the target compound (4.13 g).

Example 27

4N HCl/ethyl acetate (60 mL) was added to the compound (4.0 g) obtained in Example 26, and the resultant mixture was stirred at room temperature for 40 minutes. The solvent was removed under reduced pressure, thereby obtaining the target compound (3.7 g).

Example 28

Acetic anhydride (3 mL) and pyridine (3 mL) were added to the compound (60 mg) obtained in Example 27, and the resultant mixture was stirred overnight at room temperature. The purification was carried out in the same manner as in the Step 2 of Example 4, thereby obtaining the target compound (46 mg).

Example 29

1-methyl-cyclopropanecarboxylic acid (19 mg), WSC (36 mg), HOBt (25 mg) and triethylamine (57 µL) were added to the compound (60 mg) obtained in Example 28, and the resultant mixture was stirred overnight at room temperature. The purification was carried out in the same manner as in the Step 2 of Example 4, thereby obtaining the target compound (70 mg).

Examples 30 to 35

Using the respective reaction reagents, the target compounds were obtained in the same manner as in Example 29.

Example 36

Using the compound obtained in Example 2 and (2-bromopropyl)-carbamic acid tert-butyl ester, the target compound was obtained in the same manner as in Example 26.

Example 37

The compound obtained in Example 36 was subjected to the same treatment as in Example 27, so that the target compound was obtained.

Examples 38 to 47

The compound obtained in Example 37 was subjected to the same treatment as in Example 28, so that the target compounds were obtained.

Example 48

2,6-dimethoxybenzene sulfonyl chloride (48 mg), 2,6-lutidine (150 µL) and dichloromethane (3 mL) were added to the compound (67 mg) obtained in Example 27, and the resultant mixture was stirred overnight at room temperature. The purification was carried out in the same manner as in the Step 2 of Example 4, thereby obtaining the target compound (50 mg).

Examples 49 to 52

The compound obtained in Example 27 was subjected to the same treatment as in Example 48, so that the target compounds were obtained.

Examples 53 to 57

The target compounds were obtained in the same manner as in Example 1, Example 3 or Example 5.

Examples 58 to 63

The target compounds were obtained from the compound of Example 4, using the reaction reagents and reaction conditions shown in Example 6, Example 7, Example 8, Example 9, Example 11 and Example 23, respectively.

Example 64

The compound obtained in Example 4 was subjected to the same treatment as in Example 26, so that the target compound was obtained.

Example 65

The compound obtained in Example 64 was subjected to the same treatment as in Example 27, so that the target compound was obtained.

Example 66

Step 1

The compound (1.5 g) obtained in Example 1 was dissolved in dichloromethane (5 mL), and 1N $BBr_3$/dichloromethane (20 mL) was gradually added to the solution. The resultant reaction solution was stirred at room temperature for 15 minutes, and poured over crushed ice by decantation. After ice was completely melted, sodium hydroxide was added to the reaction solution until the reaction solution became basic. The reaction solution was then extracted with dichloromethane to obtain the desired product. The product was purified in the same manner as in the Step 2 of Example 4, so that an intermediate (1 g) was obtained.

Step 2

After the compound (100 mg) obtained in the Step 1 of Example 66, solid-supported triphenylphosphine (1.6 mmol per gram of resin, 600 mg), dichloromethane (10 mL) and ethanol (55 µL) were mixed, TMAD (165 mg) was added to the mixture, and the obtained mixture underwent a reaction at room temperature for 3 days. After the solid-supported resin was eliminated by filtration, the solvent was filtered under reduced pressure. The purification was carried out using reversed phase high performance liquid chromatography (reversed-phase HPLC), thereby obtaining the target product (40 mg).

Example 67

The compound obtained in the Step 1 of Example 66 was subjected to the same treatment as in the Step 2 of Example 66 except for the use of propanol, so that the target product was obtained. The above-mentioned Examples are summarized in Tables 1 to 8.

TABLE 1

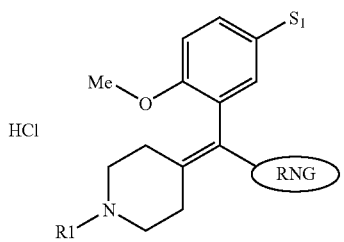

| Example | S₁ | R₁ | RNG | ESI |
|---|---|---|---|---|
| Example 1 | H | Me | 3-chlorophenyl | 328, 329, 330 |
| Example 2 | H | H | 3-chlorophenyl | 314, 316 |
| Example 3 | MeO | Me | 3-chlorophenyl | 358, 360 |

TABLE 1-continued

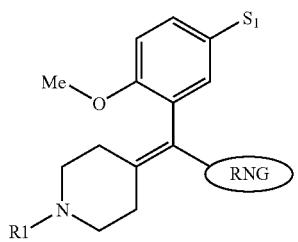

| Example | S₁ | R₁ | RNG | ESI |
|---|---|---|---|---|
| Example 4 | MeO | H | 3-chlorophenyl | 344, 345, 346 |
| Example 5 | H | Me | 2-thienyl | 300 |

TABLE 2

| Example | Alkyl halide | Reaction Conditions | R1—N | ESI |
|---|---|---|---|---|
| Example 6 | ethyl-Br | K₂CO₃/CH₃CN, RT, ON | ethyl-N | 342, 343, 344 |
| Example 7 | propyl-Br | K₂CO₃/CH₃CN, RT, ON | propyl-N | 356, 357, 358 |
| Example 8 | butyl-I | K2CO3/CH3CN, RT, ON | butyl-N | 370, 371, 372 |
| Example 9 | pentyl-I | K2CO3/CH3CN, RT, ON | pentyl-N | 384, 385, 386 |
| Example 10 | isobutyl-I | K₂CO₃/CH₃CN, 80° C., ON | isobutyl-N | 370, 371, 372 |
| Example 11 | isopentyl-I | K2CO3/CH3CN, RT, ON | isopentyl-N | 384, 385, 386 |
| Example 12 | cyclohexylmethyl-Br | K₂CO₃/CH₃CN, 80° C., ON | cyclohexylmethyl-N | 410, 411, 412 |
| Example 13 | 4-pentenyl-Br | K2CO3/CH3CN, RT, ON | 4-pentenyl-N | 382, 383, 384 |
| Example 14 | prenyl-Br | K2CO3/CH3CN, RT, ON | prenyl-N | 382, 383, 384 |
| Example 15 | cinnamyl-Br | K2CO3/CH3CN, RT, 30 min | cinnamyl-N | 430, 431, 432 |

TABLE 2-continued
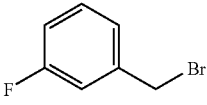
H·Cl
| Example | Alkyl halide | Reaction Conditions | R1–N | ESI |
|---|---|---|---|---|
| Example 16 | 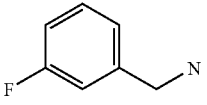 | K2CO3/CH3CN, RT, 30 min | 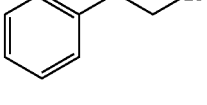 | 422, 423, 424 |
| Example 17 | 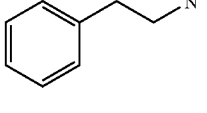 | K₂CO₃/CH₃CN, 80° C., ON | 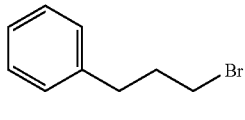 | 418, 419, 420 |
| Example 18 | 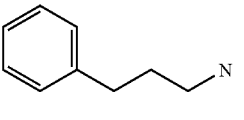 | K₂CO₃/CH₃CN, RT, ON | 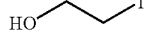 | 432, 433, 434 |
| Example 19 | 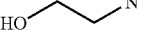 | K₂CO₃/CH₃CN, RT, ON | 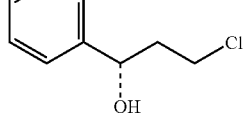 | 358, 359, 360 |
| Example 20 | 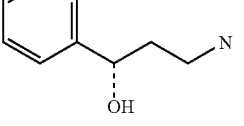 | K₂CO₃/CH₃CN, 80° C., ON | 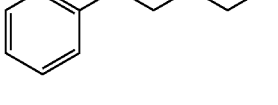 | 448, 449, 450 |
| Example 21 | 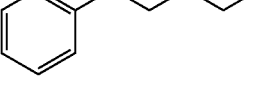 | K₂CO₃/CH₃CN, RT, ON | 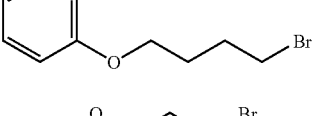 | 448, 449, 450 |
| Example 22 | 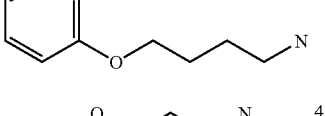 | K₂CO₃/CH₃CN, RT, ON | 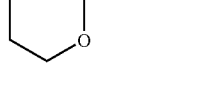 | 462, 463, 464 |
| Example 23 | 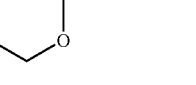 | K2CO3/CH3CN, RT, ON | 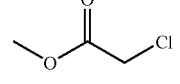 | 428, 429, 430 |
| Example 24 | 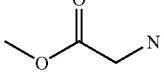 | K₂CO₃/CH₃CN, RT, ON | 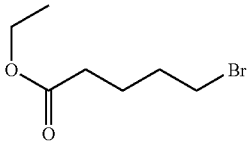 | 386, 388 |
| Example 25 | 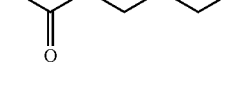 | K2CO3/CH3CN, RT, ON | | 414, 415, 416 |

TABLE 3

Structure: R-C(=O)-NH-CH2-CH2-N(piperidine)=C(2-methoxyphenyl)(3-chlorophenyl) · HCl

| Example | R-CHO | ESI |
|---|---|---|
| Example 26 | tert-butyl formate (OC(CH3)3-C(=O)-) | 457, 458, 459, 460 |
| Example 27 | H | 357, 358, 359 |
| Example 28 | ethanal (CH3CH2-C(=O)-) | 399, 400, 401 |
| Example 29 | 1-methylcyclopropanecarbaldehyde | 439, 440, 441 |
| Example 30 | pent-4-ynal | 431, 438, 438 |
| Example 31 | 1-methylcyclohexanecarbaldehyde | 481, 482, 483 |
| Example 32 | cyclohex-3-ene-1-carbaldehyde | 465, 466, 467 |
| Example 33 | thiophene-2-carbaldehyde | 4&1, 468, 469 |
| Example 34 | 3-(pyridin-3-yl)propanal | 490, 492 |

TABLE 3-continued

| Example | R-CHO | ESI |
|---|---|---|
| Example 35 | (E)-3-(2-fluorophenyl)acrylaldehyde | 505, 506, 507 |

TABLE 4

Structure: R-C(=O)-NH-CH2-CH2-CH2-N(piperidine)=C(2-methoxyphenyl)(3-chlorophenyl) · HCl

| Example | R-CHO | ESI |
|---|---|---|
| Example 36 | tert-butyl formate | 471, 472, 413 |
| Example 37 | H | 371, 373 |
| Example 38 | 1-methylcyclopropanecarbaldehyde | 453, 454, 455 |
| Example 39 | 1-phenylcyclopropanecarbaldehyde | 515, 516, 517 |
| Example 40 | 1-methylcyclohexanecarbaldehyde | 495, 496, 497 |

TABLE 4-continued

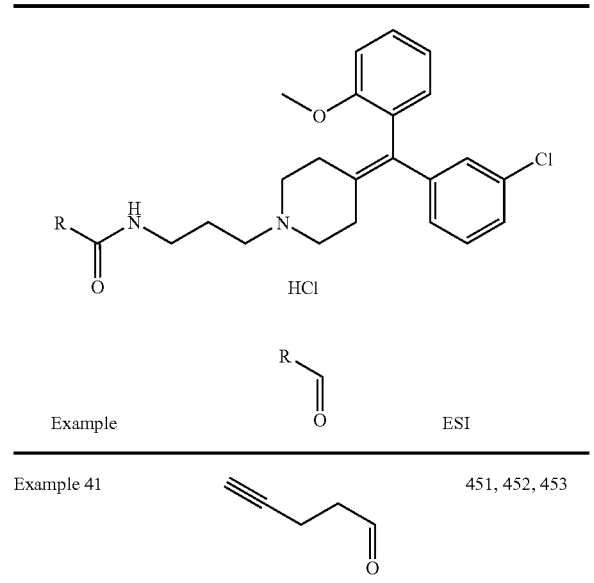

HCl

| Example | R | ESI |
|---|---|---|
| Example 41 | <img alkyne-aldehyde> | 451, 452, 453 |
| Example 42 | <img thiophene-2-carbaldehyde> | 481, 482, 483 |
| Example 43 | <img furan-3-carbaldehyde> | 465, 466, 467 |
| Example 44 | <img 4-chlorobenzaldehyde> | 509, 511 |
| Example 45 | <img cyclohexene-carbaldehyde> | 479, 480, 481 |
| Example 46 | <img benzodioxole-acetaldehyde> | 533, 534, 535 |
| Example 47 | <img naphthyl-acetaldehyde> | 539, 540, 541 |

TABLE 5

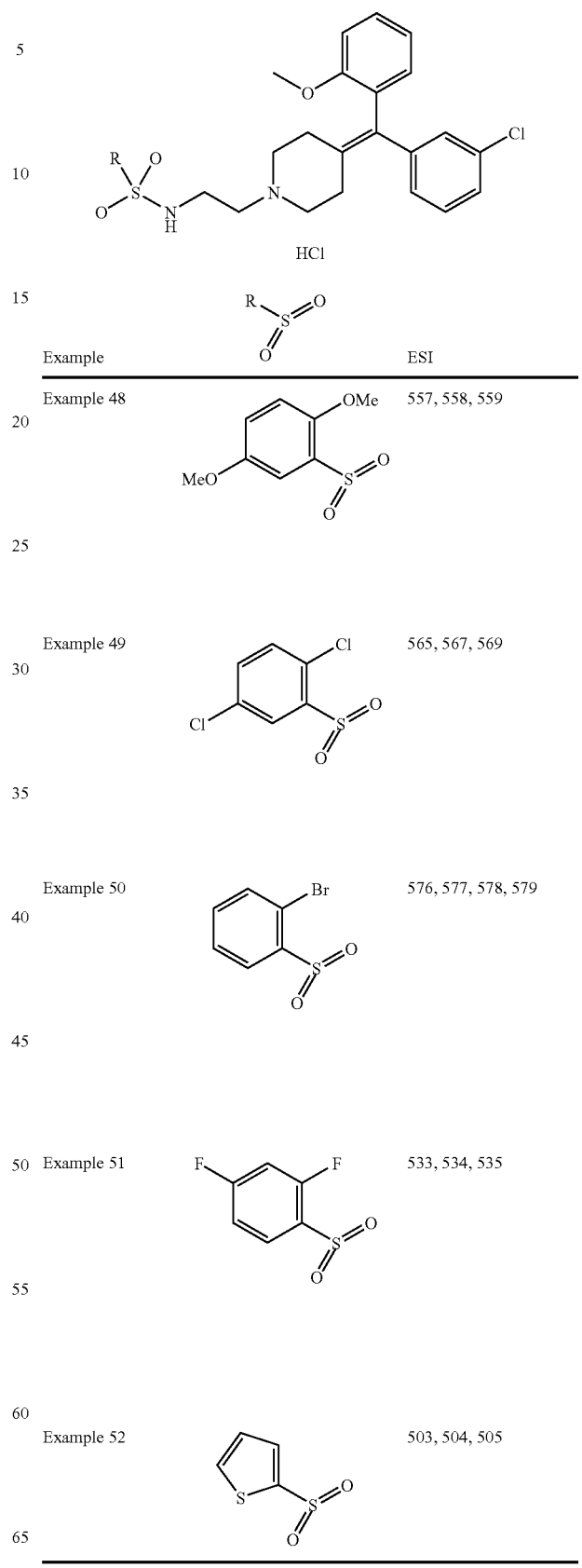

HCl

| Example | R—S(=O)₂— | ESI |
|---|---|---|
| Example 48 | 2,5-dimethoxyphenylsulfonyl | 557, 558, 559 |
| Example 49 | 2,5-dichlorophenylsulfonyl | 565, 567, 569 |
| Example 50 | 2-bromophenylsulfonyl | 576, 577, 578, 579 |
| Example 51 | 2,4-difluorophenylsulfonyl | 533, 534, 535 |
| Example 52 | thiophene-2-sulfonyl | 503, 504, 505 |

TABLE 6
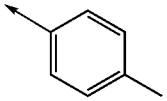
| Example | S1 | RNG | ESI |
|---|---|---|---|
| Example 53 | H | 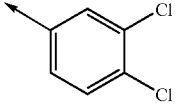 | 308 |
| Example 54 | H | 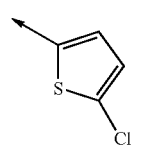 | 362, 364 |
| Example 55 | H | 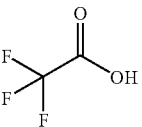 | 334, 336 |
| Example 56 | H | 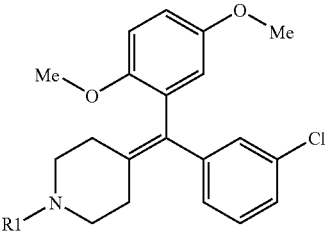 | 314 |
| Example 57 | Me |  | 342, 344 |
TABLE 7
| Example | R1 | ESI |
|---|---|---|
| Example 58 |  | 312, 373, 374 |
| Example 59 |  | 386, 387, 378 |
| Example 60 |  | 400, 401, 402 |
| Example 61 |  | 414, 415, 416 |
| Example 62 | 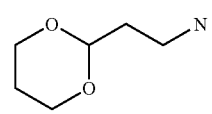 | 414, 415, 416 |
| Example 63 | 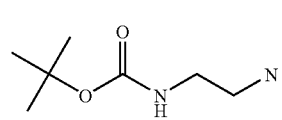 | 458, 459, 460 |
| Example 64 | 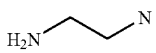 | 487, 488, 489 |
| Example 65 | 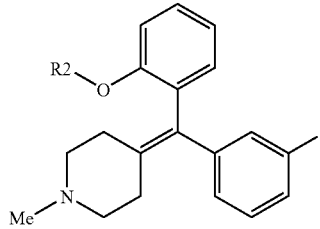 | 387, 389 |
TABLE 8
| Example | R2—O | ESI |
|---|---|---|
| Example 66 |  | 342, 343, 344 |

TABLE 8-continued

[Chemical structure: piperidine compound with R2-O-phenyl, 3-chlorophenyl, N-Me, HCl salt]

| Example | R2-O- | ESI |
|---|---|---|
| Example 67 | [propyl ether group: CH2-CH2-CH2-O-] | 356, 357, 358 |

Test Example 1

Receptor Binding Assay (RBA) Using 5HT-7 Expression Cells

Human 5-HT$_{7a}$ receptor expression CHO—K1 cells (Euroscreen; h5HT$_7$-C1 cells, No. ES-317-C) were cultured in an incubator (CO$_2$: 5%) at 37° C., using Ham's F-12 culture medium containing 400 μg/ml G418, 100 U/ml penicillin, 100 μg/ml streptomycin, and 10% fetal bovine serum. After removal of the culture medium, the cells were washed with phosphate-buffered saline (PBS(−)) free of Ca$^{2+}$ and Mg$^{2+}$, and then peeled away from a petri dish using HMEE buffer (20 mM HEPES-KOH (pH7.4), 1 mM EDTA, 1 mM EGTA, 2 mM MgCl$_2$). The cells thus collected were homogenized on ice using a Teflon homogenizer, centrifuged at 1,500×g for 5 minutes at 4° C., and the resultant supernatant liquid was then recovered. The supernatant liquid was further centrifuged at 12,000×g for 30 minutes at 4° C. The resultant precipitate was suspended in a HMEE buffer and the resultant suspension was dispensed and flash-frozen in liquid nitrogen. Thus, the frozen product was maintained at −80° C. and melted at room temperature when used in practice. In a 96-well polystyrene round-bottom plate (Falcon, No. 351190), a membrane preparation, the test compound, and 2-[$^{125}$I]-(+)-iodo-lysergic acid diethylamide (Perkin Elmer Life Science, No. NEX199) were reacted at room temperature for 3 hours in 50 μL of a binding buffer (50 mM HEPES-NaOH (pH7.4), 1 mM CaCl$_2$, 5 mM MgCl$_2$, 0.5% BSA) in each well. After completion of the reaction, the mixture was trapped by suction into a 96-well GF/B Unifilter plate (Perkin Elmer Life Science, No. 6005177), 50 μL of 0.05% polyethyleneimine being previously added to each well. Each well of the above-mentioned Unifilter plate was washed with about 200 μL of a washing buffer (50 mM HEPES-NaOH (pH7.4), 1 mM CaCl$_2$, 5 mM MgCl$_2$, 0.5 M NaCl, 0.05% Tween-20) three times, and dried overnight. Then, 30 μL of Microscint (Packard, No. NR6013611) was added to each well. The amount of bound 2-[$^{125}$I]-(+)-iodo-lysergic acid diethylamide was determined using Top Counter (Packard). The count obtained when 100 μM of crozapine was used as the test compound was fixed at 0%, while the count obtained when no compound was added was fixed at 100%. The binding ratios of 2-[$^{125}$I]-(+)-iodo-lysergic acid diethylamide obtained at varied concentrations of the compound were expressed by percentage (%), and the relationship between the concentration of each compound and the binding ratio (%) was approximated to a sigmoid curve. A concentration of the compound corresponding to the binding ratio 50% of 2-[$^{125}$I]-(+)-iodo-lysergic acid diethylamide was defined as the value of IC50.

The test results thus obtained are shown in Table 9.

TABLE 9

| Example | pIC50 |
|---|---|
| Example 1 | 7.4 |
| Example 2 | 7.9 |
| Example 3 | 8.0 |
| Example 4 | 7.7 |
| Example 5 | 8.2 |
| Example 7 | 7.5 |
| Example 36 | 7.0 |
| Example 48 | 8.2 |
| Example 49 | 8.0 |
| Example 50 | 7.8 |
| Example 51 | 7.4 |
| Example 52 | 7.4 |
| Example 53 | 7.6 |
| Example 54 | 7.5 |
| Example 55 | 7.4 |
| Example 56 | 7.4 |
| Example 57 | 7.5 |
| Example 58 | 7.8 |
| Example 59 | 8.3 |
| Example 60 | 7.0 |

Test Example 2

Evaluation of 5HT-7 Agonist Activity Using 5HT-7 Expression Cells

Human 5HT-7 expression CHO—K1 cells, "h5HT7-C2" were purchased from Euroscreen SA. The h5HT7-C2 cells were suspended in a culture medium (GIBCO CHO-SFM-II, Clontech) containing 1% fetal bovine serum at a concentration of 2×10$^5$ cells/mL. 100 μL of the suspension was inoculated in a 96-well plate and cultured in a CO$_2$ incubator at 37° C. for 5 hours. After the culture medium was removed by suction, each well was washed with 200 μl of CHO-SFM-II medium, and then 100 μL of CHO-SFM-II medium was added to each well and the cultures were further grown overnight at 37° C. in a CO$_2$ incubator. After the culture medium was removed by suction, 100 μL of a RPMI-1640 culture medium containing 1 mM 3-isobutyl-1-methylxanthine (IBMX) and the compound was added and stimulated in a CO$_2$ incubator at 37° C. After stimulation, the culture medium was removed by suction and the cultures were shaken with the addition of 100 μL of 0.1N hydrochloric acid and allowed to stand at 4° C. for one hour. A 50 μL aliquot of the 0.1N hydrochloric acid solution was taken out of each well and dried under reduced pressure. Then, the cAMP concentration was determined using a cAMP EIA kit (RPN225, Amersham) by the method in conformity of the attached protocol (Protocol 2. Acetylation EIA Procedure). The cAMP concentration obtained when 10 μM of serotonin was used as the test compound was fixed at 100%, while the cAMP concentration obtained when no compound was added was fixed at 0%. The cAMP concentrations obtained with varied concentrations of the compound were expressed by percentage (%), and the relationship between the concentration of each compound and the cAMP (%) was approximated to a sigmoid curve. A concentration of the compound corresponding to the cAMP value that is a half the maximum value (Emax) on the approximated sigmoid curve was defined as the value of EC50.

The test results thus obtained are shown in Table 10 and FIG. 1.

TABLE 10

| Example | EC50 (µM) |
|---|---|
| Example 3 | 0.099 |
| Example 4 | 0.087 |
| Example 59 | 0.023 |

As is also apparent from FIG. 1, the action of the compound obtained in Example 59 was stronger than that of serotonin, i.e., an agonist in vivo.

As previously mentioned, the compounds of the present invention can exhibit excellent effectiveness as the 5-HT7 agonist.

Test Example 3

Evaluation of the Action of Test Compounds on in-vivo Mouse Model of Bowel Movement Induced by 5-hydroxytryptophan (5-HTP)

The compound obtained in Example 5 was used as the test compound, the action of which was evaluated using in-vivo mice model of bowel movement induced by 5-hydroxytryptophan (5-HTP) according to the method of G. J. Sanger et al., (British Journal of Pharmacology, 130: 706-712, 2000). Six-week-old SLC:ICR male mice were transferred to a five-compartment stainless steel mouse cage and acclimatized for one hour or more. Then, the test compound was orally administered to the mice at a dose of 30 mg/kg (n=10). Thirty minutes later, 5-HTP was given by subcutaneous administration at a dose of 10 mg/mL/kg, while physiological saline was administered at a dose of 5 mL/kg of to the control group to which 5-HTP was not administered. Immediately after that, the state of stool discharged from the individual was observed over a period of 30 minutes. The state of stool was expressed by the score "0" where normal stool or no stool was observed, or "1" where watery or loose stool was observed. The inhibition ratio (%) of the test compound was calculated assuming that the score value obtained by subtracting the scores of the medium group to which no 5-HTP was administered from the scores of the medium group to which 5-HTP was administered was fixed at 100%. The result was that the inhibition ratio of the test compound was 100%. As can be seen from the results, the 5-HT7 receptor antagonist of the present invention can exhibit excellent effectiveness as the agent for treating the irritable bowel syndrome of diarrhea type.

Test Example 4

Evaluation of 5HT-7 Antagonist Activity Using 5HT-7 Expression Cells

Human 5HT-7 expression CHO—K1 cells, "h5HT7-C2" were purchased from Euroscreen SA. The h5HT7-C2 cells were suspended in a culture medium (GIBCO CHO-SFM-II, Clontech) containing 1% fetal bovine serum at a concentration of of $2 \times 10^5$ cells/mL. 100 µL of the suspension was inoculated in a 96-well plate and cultured in a $CO_2$ incubator at 37° C. for 5 hours. After the culture medium was removed by suction, each well was washed with 200 µL of CHO-SFM-II medium, and then 100 µL of CHO-SFM-II medium was added to each well, and the cultures were further grown overnight at 37° C. in a $CO_2$ incubator. After the culture medium was removed by suction, 50 µL of a RPMI-1640 culture medium containing 1 mM 3-isobutyl-1-methylxanthine (IBMX) and the compound was added. Approximately 5 minutes later, 50 µL of a RPMI-1640 culture medium containing 1 mM IBMX and serotonin (0.2 µM) was further added, and the cultures were stimulated in a $CO_2$ incubator at 37° C. for 30 minutes. After stimulation, the culture medium was removed by suction and the cultures were shaken with the addition of 50 µL of 0.1N hydrochloric acid and allowed to stand at 4° C. for one hour. A 40 µL aliquot of the 0.1N hydrochloric acid solution was taken out of each well and dried under reduced pressure. Then, the cAMP concentration was determined using a DELFIA cAMP kit (CR89-102, PerkinElmer) according to the method in conformity of the attached protocol. The inhibition activity of the compound was calculated assuming that the cAMP concentration obtained when no compound was added was regarded as inhibition ratio of 0%, and the cAMP concentration obtained when serotonin was not added was regarded as inhibition ratio of 100%. The IC50 of the compound obtained in Example 5 was found to be 6.0 nM.

Test Example 5

Action on Mice Model of Writhing Induced by Acetic Acid

This evaluation was carried out by the method in accordance with Matsumoto et al., (Eur J Pharmacol., 352, 47, (1998)).

The effects of the test compound 1 in the acetic acid writhing tests were examined using 4-week-old ICR male mice. A 0.9% acetic acid solution (diluted with physiological saline) was given to the mice by intraperitoneal administration. After a lapse of 5 minutes, the number of writhing was recorded for 15 minutes. The test compound suspended in a 0.5% tragacanth solution had been orally administered to the mice at a dose of 5 mL/kg 90 minutes before acetic acid was given. The inhibition ratio was found to be 49% when the compound of Example 5 was administered at a 10 mg/kg dose.

The result shows that the 5-HT7 receptor antagonist according to the present invention can exhibit excellent effectiveness as the agent for treating the visceral pain and abdominal pain.

The invention claimed is:

1. A piperidine compound represented by formula (1) or pharmaceutically acceptable salt thereof:

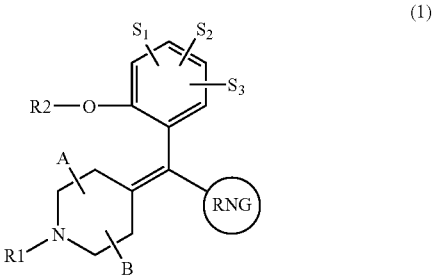

(1)

wherein $S_1$, $S_2$ and $S_3$, which may be the same or different, are each a hydrogen atom, halogen atom, hydroxyl group, lower alkyl group, lower alkenyl group, lower alkynyl group, cyclic alkyl group which may have a hetero atom in the ring thereof, aryl group, heteroaryl group, lower alkyl group substituted by cyclic alkyl group which may have a hetero atom in the ring thereof, lower alkyl group substituted by aryl group, lower alkyl group substituted by heteroaryl group, lower alkoxyl group, lower alkylthio group, lower alkoxyl group substituted by cyclic alkyl group which may have a hetero atom in the ring thereof, lower alkylthio group substituted by cyclic alkyl group which may have a hetero atom in the ring thereof, lower alkoxyl group substituted by aryl group, lower alkylthio group substituted by aryl group, lower alkoxyl group substituted by heteroaryl group, lower alkylthio group substituted by heteroaryl group, cyclic alkyloxy group which may have a hetero atom in the ring thereof, aryloxy group, heteroaryloxy group, hydroxy-lower alkyl group, hydroxy-lower alkenyl group, hydroxy-lower alkoxyl group, halogenated lower alkyl group, halogenated lower alkoxyl group, halogenated lower alkylthio group, halogenated lower alkenyl group, nitro group, cyano group, substituted or unsubstituted amino group, carboxyl group, lower alkyloxycarbonyl group, substituted or unsubstituted carbamoyl group, lower alkanoyl group, aroyl group, lower alkylsulfonyl group, or substituted or unsubstituted sulfamoyl group; or $S_1$, $S_2$ and $S_3$ may form a ring in combination, which may contain one or two hetero atoms independently selected from oxygen atoms nitrogen atoms, and sulfur atoms in the ring thereof; wherein the heteroaryl groups of $S_1$, $S_2$ and $S_3$ are independently selected from the group consisting of pyridyl groups, pyrazyl groups, pyrimidyl groups, pyrazolyl groups, pyrrolyl groups, triazyl groups, furyl groups, thienyl groups, isoxazolyl groups, isothiazolyl groups, indolyl groups, guinolyl groups, isoguinolyl groups, and benzimidazolyl groups;

RNG is a substituted or unsubstituted aryl group, or a substituted or unsubstituted heteroaryl group containing one, two, three or four hetero atoms selected from the group consisting of oxygen atom, sulfur atom and nitrogen atom; wherein the heteroaryl group of RNG is selected from the group consisting of pyridyl group, pyrazyl group, pyrimidyl group, pyrazolyl group, pyrrolyl group, triazyl group, furyl group, thienyl group, isoxazolyl group, isothiazolyl group, indolyl group, guinolyl group, isoguinolyl group, and benzimidazolyl group;

$R^1$ is a hydrogen atom; hydroxyl group; lower alkyl group; lower alkenyl group; lower alkynyl group; cyclic alkyl group which may have a hetero atom in the ring thereof; aryl group; heteroaryl group; lower alkyl group substituted by cyclic alkyl group which may have a hetero atom in the ring thereof; lower alkyl group substituted by aryl group; lower alkenyl group substituted by aryl group; lower alkyl group substituted by heteroaryl group; lower alkyl group substituted by lower alkoxyl group; lower alkyl group substituted by amino group; lower alkyl group substituted by carboxyl group; lower alkyl group substituted by carbonyl group which is substituted by lower alkoxyl group; lower alkoxyl group; hydroxy-lower alkyl group; hydroxy-lower alkenyl group; hydroxy-lower alkyl group substituted by aryl group; halogenated lower alkyl group; halogenated lower alkenyl group; lower alkyl group substituted by amide group, which may be substituted by any of cyclic alkyl group where a hetero atom may be included in the ring thereof, aryl group, heteroaryl group, lower alkyl group, lower alkynyl group, lower alkoxyl group, lower alkyl group substituted by aryl group, lower alkyl group substituted by heteroaryl group, lower alkenyl group substituted by aryl group, lower alkenyl group substituted by heteroaryl group, lower alkynyl group, cyclic alkenyl group or piperonyl group; lower alkyl group substituted by sulfonamide group, which may be substituted by any of cyclic alkyl group where a hetero atom may be included in the ring thereof, aryl group, heteroaryl group, lower alkyl group, lower alkynyl group, lower alkoxyl group, lower alkyl group substituted by aryl group, lower alkyl group substituted by heteroaryl group, lower alkenyl group substituted by aryl group, lower alkenyl group substituted by heteroaryl group, lower alkynyl group, or cyclic alkenyl group; or lower alkyl group substituted by urea group, which may be substituted by any of cyclic alkyl group where a hetero atom may be included in the ring thereof, aryl group, heteroaryl group, lower alkyl group, lower alkynyl group, lower alkoxyl group, lower alkyl group substituted by aryl group, lower alkyl group substituted by heteroaryl group, lower alkenyl group substituted by aryl group, lower alkenyl group substituted by heteroaryl group, lower alkynyl group, cyclic alkenyl group or piperonyl group; wherein said heteroaryl groups substituted on R1 are independently selected from the group consisting of furan, thiophene, pyridine, dioxane, and benzodioxane;

$R^2$ is a lower alkyl group, lower alkenyl group, lower alkynyl group, halogenated lower alkyl group, halogenated lower alkenyl group, or halogenated lower alkynyl group; and A and B, which may be the same or different, are each a hydrogen atom, halogen atom or lower alkyl group, provided that the following compounds (i) through (iv) are excluded:

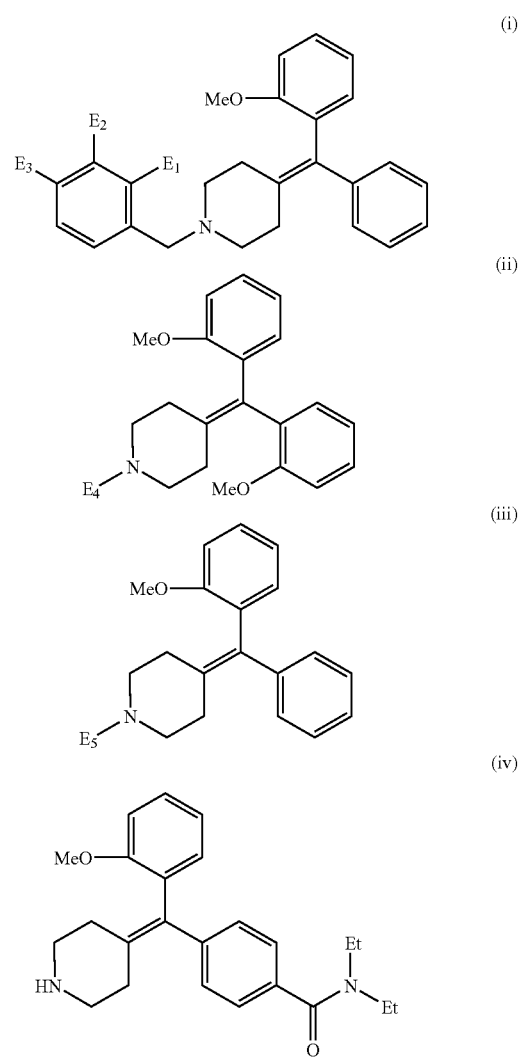

wherein (i) $E_1$ is H—, HO— or PhCOO—; $E_2$ is H—, HO— or PhCOO—; and $E_3$ is H—, HO—, PhCOO— or tert-butyl;

(ii) $E_4$ is methyl group or propylene group having a substituent at the 3-position; (iii) $E_5$ is HO—CH$_2$CH$_2$—, HO—CH$_2$CH$_2$OCH$_2$CH$_2$—, or H—; and (iv) compound is resented by formula (iv).

2. The piperidine compound or pharmaceutically acceptable salt thereof as claimed in claim 1, wherein $R^2$ in the formula (1) is a lower alkyl group or halogenated lower alkyl group.

3. The piperidine compound or pharmaceutically acceptable salt thereof as claimed in claim 1, wherein $R^2$ in the formula (1) is methyl group.

4. The piperidine compound or pharmaceutically acceptable salt thereof as claimed in claim 1, wherein $S_1$, $S_2$ and $S_3$ in the formula (1) may be the same or different and each represents a hydrogen atom, halogen atom, hydroxyl group, lower alkyl group, lower alkenyl group, lower alkynyl group, lower alkoxyl group, lower alkylthio group, hydroxy-lower alkyl group, hydroxy-lower alkenyl group, hydroxy-lower alkoxyl group, halogenated lower alkyl group, halogenated lower alkoxyl group, halogenated lower alkylthio group, halogenated lower alkenyl group, or substituted or unsubstituted amino group.

5. The piperidine compound or pharmaceutically acceptable salt thereof as claimed in claim 4, wherein $R^2$ in the formula (1) is a lower alkyl group or halogenated lower alkyl group.

6. The piperidine compound or pharmaceutically acceptable salt thereof as claimed in claim 4, wherein $R^2$ in the formula (1) is methyl group.

7. The piperidine compound or pharmaceutically acceptable salt thereof as claimed in claim 4, wherein, in the formula (1), $S_1$, $S_2$ and $S_3$ may be the same or different and each represents a hydrogen atom, halogen atom, lower alkyl group, lower alkoxyl group, lower alkylthio group, halogenated lower alkyl group, halogenated lower alkoxyl group or halogenated lower alkylthio group; $R^2$ is methyl group; and A and B represent hydrogen atom.

8. The piperidine compound or pharmaceutically acceptable salt thereof as claimed in claim 1, wherein the compound represented by the formula (1) is selected from the group consisting of the following compounds (2-1) to (2-4):

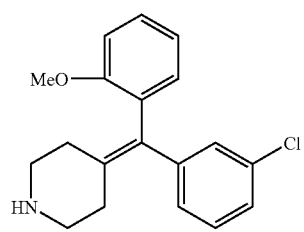

(2-1)

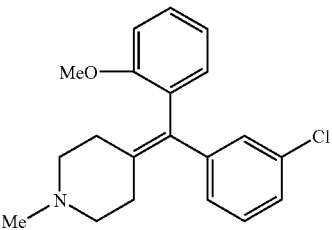

(2-2)

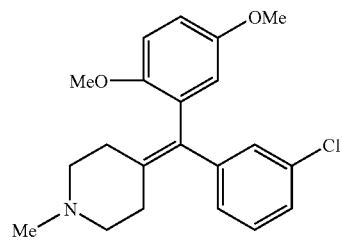

(2-3)

-continued

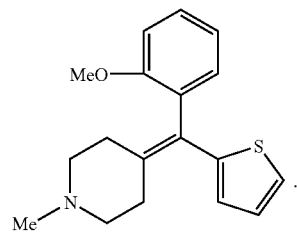

(2-4)

9. The piperidine compound or pharmaceutically acceptable salt thereof as claimed in claim 1, wherein the compound represented by the formula (1) is a compound of formula (2-5):

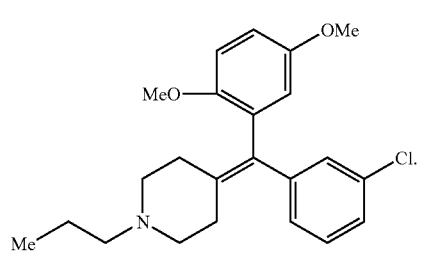

(2-5)

10. The piperidine compound or pharmaceutically acceptable salt thereof as claimed in claim 1, wherein the compound represented by the formula (1) is selected from the group consisting of the following compounds (3-1) to (3-4):

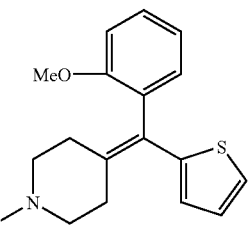

(3-1)

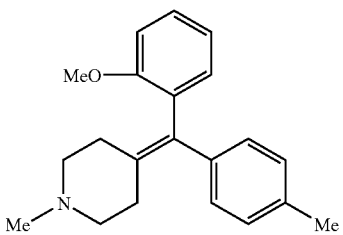

(3-2)

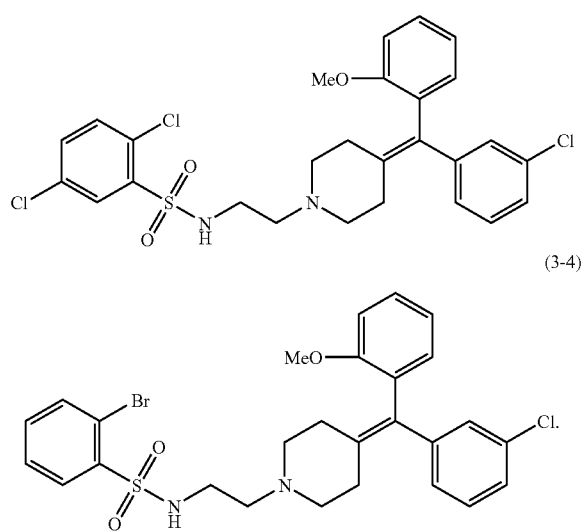

11. A pharmaceutical composition comprising as the active substance the piperidine compound or pharmaceutically acceptable salt thereof as claimed in claim 1.

12. A method for treating irritable bowel syndrome in a patient comprising administering the piperidine compound or pharmaceutically acceptable salt thereof as claimed in claim 1 to a patient in need thereof.

13. The method for treating irritable bowel syndrome as claimed in claim 12, wherein the irritable bowel syndrome is of diarrhea type.

14. The method for treating irritable bowel syndrome as claimed in claim 12, wherein the irritable bowel syndrome is of constipation type.

15. The method for treating irritable bowel syndrome as claimed in claim 12, wherein the irritable bowel syndrome is of alternate type.

16. A method for treating visceral pain or abdominal pain in a patient comprising administering as the active substance the piperidine compound or pharmaceutically acceptable salt thereof as claimed in claim 1 to a patient in need thereof, wherein the visceral pain or abdominal pain is associated with 5-HT7 activity.

* * * * *

UNITED STATES PATENT AND TRADEMARK OFFICE
CERTIFICATE OF CORRECTION

PATENT NO. : 7,683,077 B2 Page 1 of 1
APPLICATION NO. : 10/557353
DATED : March 23, 2010
INVENTOR(S) : Shingo Makino et al.

It is certified that error appears in the above-identified patent and that said Letters Patent is hereby corrected as shown below:

Column 37, Claim 1, Line 25
Please delete "guinolyl"
and replace with -- quinolyl --

Column 37, Claim 1, Line 25
Please delete "isoguinolyl"
and replace with -- isoquinolyl --

Column 37, Claim 1, Line 36
Please delete "guinolyl"
and replace with -- quinolyl --

Column 37, Claim 1, Line 36
Please delete "isoguinolyl"
and replace with -- isoquinolyl --

Signed and Sealed this

Eleventh Day of May, 2010

David J. Kappos
*Director of the United States Patent and Trademark Office*